(12) United States Patent
Huber et al.

(10) Patent No.: US 7,396,338 B2
(45) Date of Patent: Jul. 8, 2008

(54) ORTHOPAEDIC DEVICE FOR CORRECTING ABNORMAL POSITIONS OF THE TOES

(75) Inventors: Vitus Maria Huber, München (DE); Axel Krauss, Waakirchen (DE)

(73) Assignee: Hallufix AG, München (DE)

( * ) Notice: Subject to any disclaimer, the term of this patent is extended or adjusted under 35 U.S.C. 154(b) by 68 days.

(21) Appl. No.: 10/525,852

(22) PCT Filed: Jul. 25, 2003

(86) PCT No.: PCT/EP03/08204

§ 371 (c)(1),
(2), (4) Date: Oct. 5, 2005

(87) PCT Pub. No.: WO2004/019835

PCT Pub. Date: Mar. 11, 2004

(65) Prior Publication Data

US 2006/0155233 A1     Jul. 13, 2006

(30) Foreign Application Priority Data

Aug. 30, 2002   (DE) ................................ 102 40 121

(51) Int. Cl.
*A61F 5/00*      (2006.01)
*A61F 13/06*     (2006.01)
(52) U.S. Cl. ........................... 602/30; 602/23; 128/893; 128/894
(58) Field of Classification Search ............... 602/23, 602/30; 128/893, 894; 2/21, 239
See application file for complete search history.

(56) References Cited

U.S. PATENT DOCUMENTS

| 933,423 | A | | 9/1909 | De Ford | |
|---|---|---|---|---|---|
| 1,055,810 | A | * | 3/1913 | Scholl | 602/30 |
| 1,183,062 | A | * | 5/1916 | De Ford | 602/30 |
| 1,213,786 | A | * | 1/1917 | Wilms | 602/30 |
| 2,596,038 | A | * | 5/1952 | Mayer | 602/30 |
| 3,219,032 | A | * | 11/1965 | Levitt | 602/30 |
| 5,542,774 | A | | 8/1996 | Hoy | |
| 5,897,515 | A | * | 4/1999 | Willner et al. | 602/27 |
| 6,001,075 | A | * | 12/1999 | Clemens et al. | 602/16 |
| 6,254,559 | B1 | * | 7/2001 | Tyrrell | 602/16 |
| 7,200,875 | B2 | * | 4/2007 | Dondero | 2/436 |

FOREIGN PATENT DOCUMENTS

| DE | 299 08 981 | 1/2000 |
|---|---|---|
| DE | 298 24 735 | 7/2002 |
| DE | 202 05 091 | 9/2002 |

* cited by examiner

*Primary Examiner*—Justine R Yu
*Assistant Examiner*—Kristen C Matter
(74) *Attorney, Agent, or Firm*—Pauley Petersen & Erickson

(57) ABSTRACT

The invention concerns an orthopaedic device for the correction of incorrectly positioned toes, having a fastening provision (8a) in the region of the big toe, a fastening provision (8b) in the region of the central foot and a flexible splint (9), extends between the fastening provisions (8a, 8b) along the inner side of the foot, and in which the flexible splint (9) is formed as a hinged splint, articulated in the direction of flexion and extension of the toe or toes.

51 Claims, 20 Drawing Sheets

ORTHOPAEDIC DEVICE FOR CORRECTING ABNORMAL POSITIONS OF THE TOES

FIELD OF THE INVENTION

The invention concerns an orthopaedic device for the correction of wrongly positioned toes.

BACKGROUND OF THE INVENTION

A foot-binder for the treatment of incorrect positioning of the big toe, for example of hallux valgus, is known from DE 100 34 354 A1. It features a holder for the big toe, extensible in the foot's longitudinal direction, and connected at a free end to an annular binding surrounding the central region of the foot, with the result that a corrective force acts on the big toe in the direction of the anatomically correct toe position.

BRIEF SUMMARY OF THE INVENTION

Experience has shown that patients wear such devices only reluctantly and unreliably, because they are found to be obtrusive, to be a nuisance when worn with ordinary shoes, or even, when worn for long periods, to be tiresome or painful. The success of treatment through the use of this type of binding is therefore not assured.

A pad splint is known from DE 1 881 215 U1, running along the inner side of the foot acting as a spring, and having a ring-eye at the toe end that is used to hold the big toe. At the other end the pad splint is curved, allowing it to be placed against the heel. This allows a big toe to be brought into the normal position out of an inwardly bent and incorrect toe position. This splint has significant disadvantages. For instance it is found by those who wear it to be extremely uncomfortable in use, with the result that it is only very reluctantly worn and the consequence that the success of the treatment is not ensured.

A device for the treatment of big toes is known from the German registered utility model DE 8 902 545.8 U1, having a stocking with a pouch that surrounds the big toe and with a splint running along the inner side of the foot, held in a pocket sewn onto the stocking. This kind of device for treating big toes is intended for nocturnal treatment or when the patient is asleep. Its disadvantage is that the freedom of movement of the splinted big toe in the direction of flexion or extension of the big toe is inhibited. This device is therefore not suitable for long term use. Wearing this device inside a shoe is extremely uncomfortable for a patient, and heavily restricts freedom of movement.

Spreading devices are also known, taking the form of a wedge and being positioned in the space between the big toe and the second toe, so that the big toe is pushed towards the inner side of the foot. The disadvantage of these devices is that, in order to exert a force, they support themselves against the neighbouring toes, and can therefore cause or encourage incorrect positioning of the neighbouring toes.

The purpose of the invention is to provide a device with which the valgus displacement of toes, i.e. a displacement in which one or more toes are displaced toward the outer side of the foot, can be treated. It should also be possible to wear the device with comfort, and in particular without significant impairment of normal activity. This will raise the level of successful treatment in comparison with the current state of the art.

This task is performed by an orthopaedic device for the correction of incorrect toe positioning having a first fastening provision in a region of a big toe, a second fastening provision in a region of a central foot. and a flexible splint, which is held by the fastening provisions in the regions of the big toe and the central foot and which extends along an inner side of the foot wherein the flexible splint is formed as a hinged flexible splint. articulated in a direction of flexion and extension of a toe or toes requiring correction.

BRIEF DESCRIPTION OF THE DRAWINGS

Figure 1:
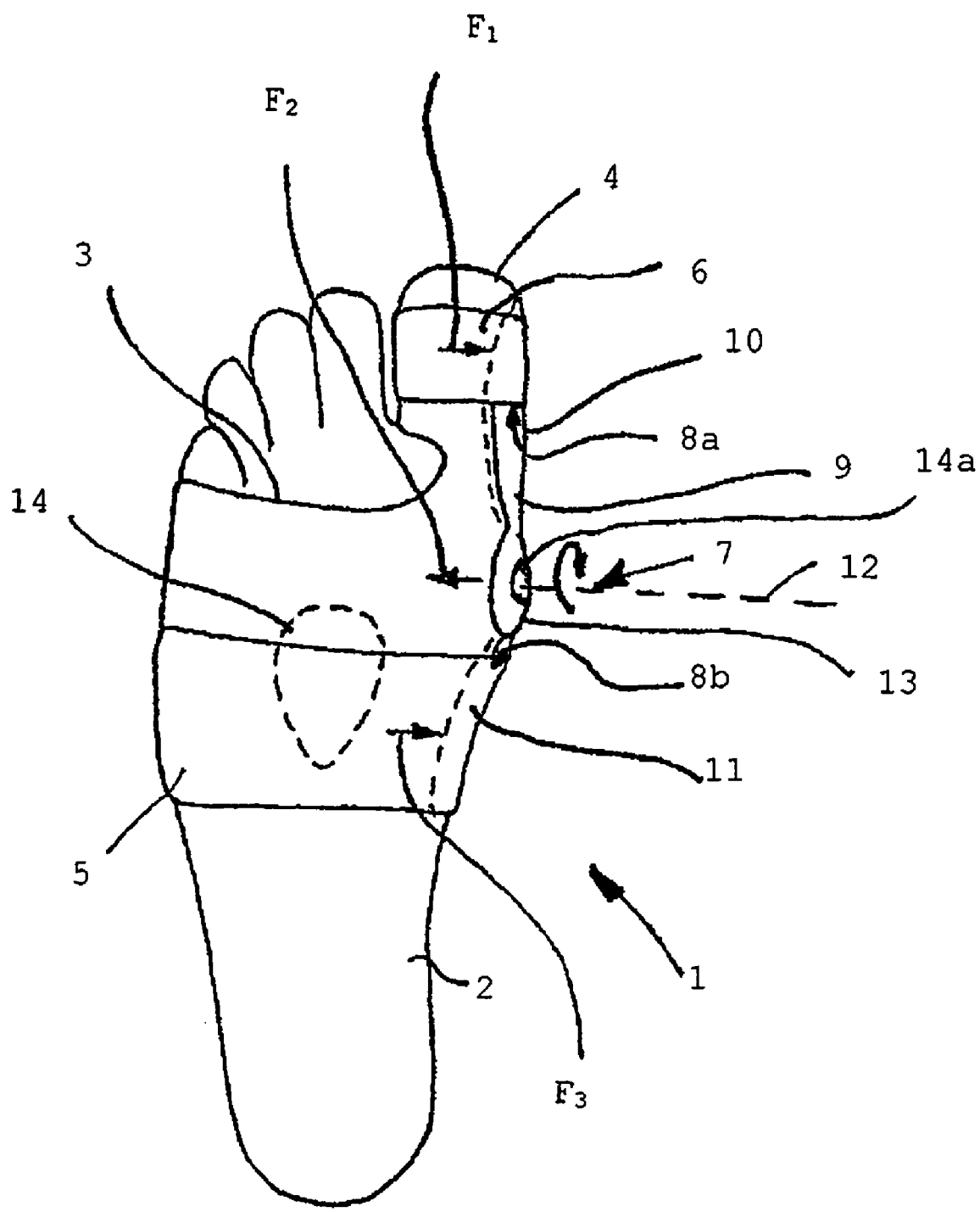
FIG. 1 A diagrammatic view from below of a first device according to the invention.

An initial embodiment of the device according to the invention 1 (FIG. 1) has an open stocking 2 in the region of the toes or a similar enclosing element for the foot. In the region of the toes the stocking 2 has an opening which is edged by a boundary 3. Further, the device according to the invention 1 includes a holder for the big toe, e.g. a toe pouch 4, which is joined in one piece with the stocking 2 or which is attached to this stocking 2. The big toe pouch 4 surrounds the circumference of the big toe, preferably entirely, and is open in the region of the free end of the toe.

Preferably, however, the big toe pouch 4 is closed at the front, as this hinders the big toe pouch 4 better from slipping relative to the big toe.

In the region of the central foot the device according to the invention 1 has a first annular binding 5 which surrounds the central foot, preferably entirely, and whose purpose requires it to be connected to the stocking 2. Advantageously, the first annular binding 5 surrounds the stocking 2 on the outside in the region of the central foot.

A second annular binding 6 is positioned surrounding the big toe pouch 4 in the area of the free end of the big toe, preferably surrounding the circumference of the big toe completely. The annular bindings 5 and 6 are favourably made from a flexible, supple material that resists circumferential stretching, i.e. in the direction of the perimeter, for example fabric tape or a non-stretching adhesive tape. In the area of the inner side of the foot 7, both the first annular binding 5 and the second annular binding 6 are, over a certain area, not joined either to the stocking 2 or to the big toe pouch 4, so that fastenings/holders 8a, 8b, e.g. push-in pockets, are formed between the annular bindings 5, 6 and the big toe pouch 4 or the stocking 2.

The inner side of the foot 7 is defined as the long side of a foot that faces the neighbouring foot. The outer side of the foot is the long side of the foot opposite the inner side.

A flexible splint 9 extends along the inner side of the foot 7 from holder 8b to holder 8a. The flexible splint 9 is formed as a hinged flexible splint, and has a first hinged splint shank 10 and a second hinged splint shank 11 which have an articulated connection via a hinge mechanism 13 and are thus able to pivot around an axis 12.

The articulated hinge mechanism 13 is arranged in respect of the stocking 2 and of the foot in such a way that the pivoting axis 12 corresponds largely to the axis of the main big toe joint in the direction of flexion and extension 20, which is the natural bending direction, i.e. the dorsal and plantar bending direction. Starting from the hinge mechanism 13, the first hinged splint shank 10 extends to holder 8a. Starting again from the hinge mechanism 13, the second hinged splint shank 11 extends to the second holder 8b. This means that the hinge mechanism 13 is positioned on patients approximately in the region of the swelling (pseudoexostosis) on the inner side of the foot typical for the hallux-valgus displacement, which often protrudes beyond the proper contour on the inner side of the foot. Wearing a device 1 according to the invention therefore exercises a force F1 acting on the inner side of the foot in the medio-lateral direction. In the region of the main big toe joint, a force F2 is exercised through the swelling in the opposite direction. A supporting force F3 resulting from the forces F1 and F2 is absorbed in holder 8b by the first annular binding 5.

In the region of the sole of the foot it is helpful to include a pad 14, in particular a foot-spreading pad, behind the main joints of the toes to provide retrocapital support. This provides supporting alignment of the transverse arch, which has an additional beneficial influence on correction of the toe displacement.

With the first embodiment in accordance with FIG. 1 with annular bindings 5, 6 it is possible and appropriate to use a normal stocking 2 or sock of ordinary woven fabric, since the annular bindings 5, 6, which resist circumferential stretching, provide sufficient force transmission.

Figure 1A:
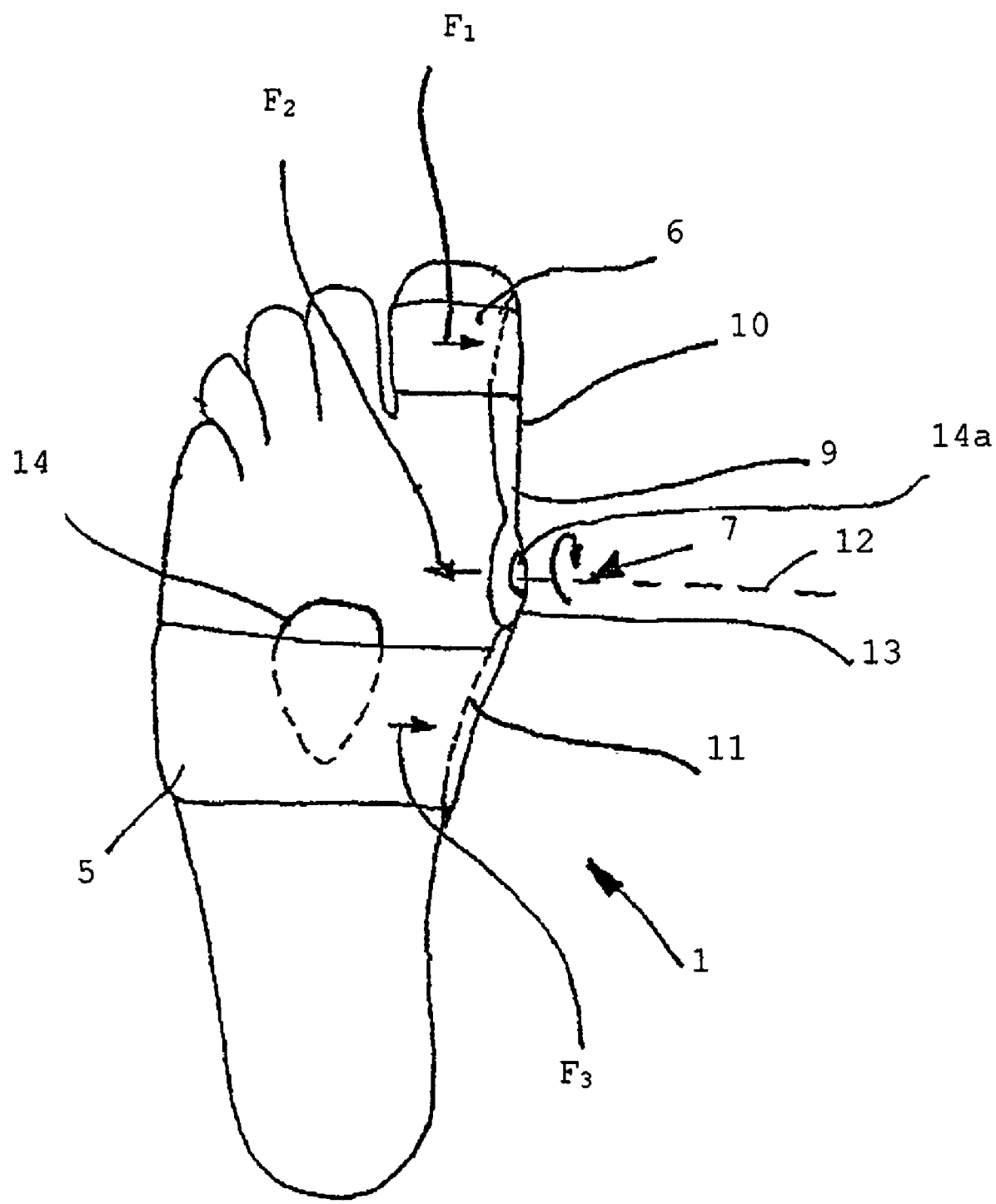

In the simplest possible particularly favourable embodiment (FIG. 1a) the device according to the invention 1 consists merely of the annular bindings 5, 6, the flexible splint 9 and possibly of the pad 14, and this means that the flexible splint 9 is at least partially in direct contact with the skin of the patient's foot. This extremely simple embodiment of the device according to the invention 1 has been found to be particularly effective, since accidental slippage of the device 1 relative to the foot of the patient is prevented precisely by the absence of the intermediate stocking layer. The result is, surprisingly, that omission of the stocking brings increased comfort. Moreover, a device 1 without a stocking represents the embodiment that is most economical to manufacture. In the embodiment according to FIG. 1a, the annular bindings 4, 5 are each attached to the associated hinged splint shank 10, 11.

Figure 2:
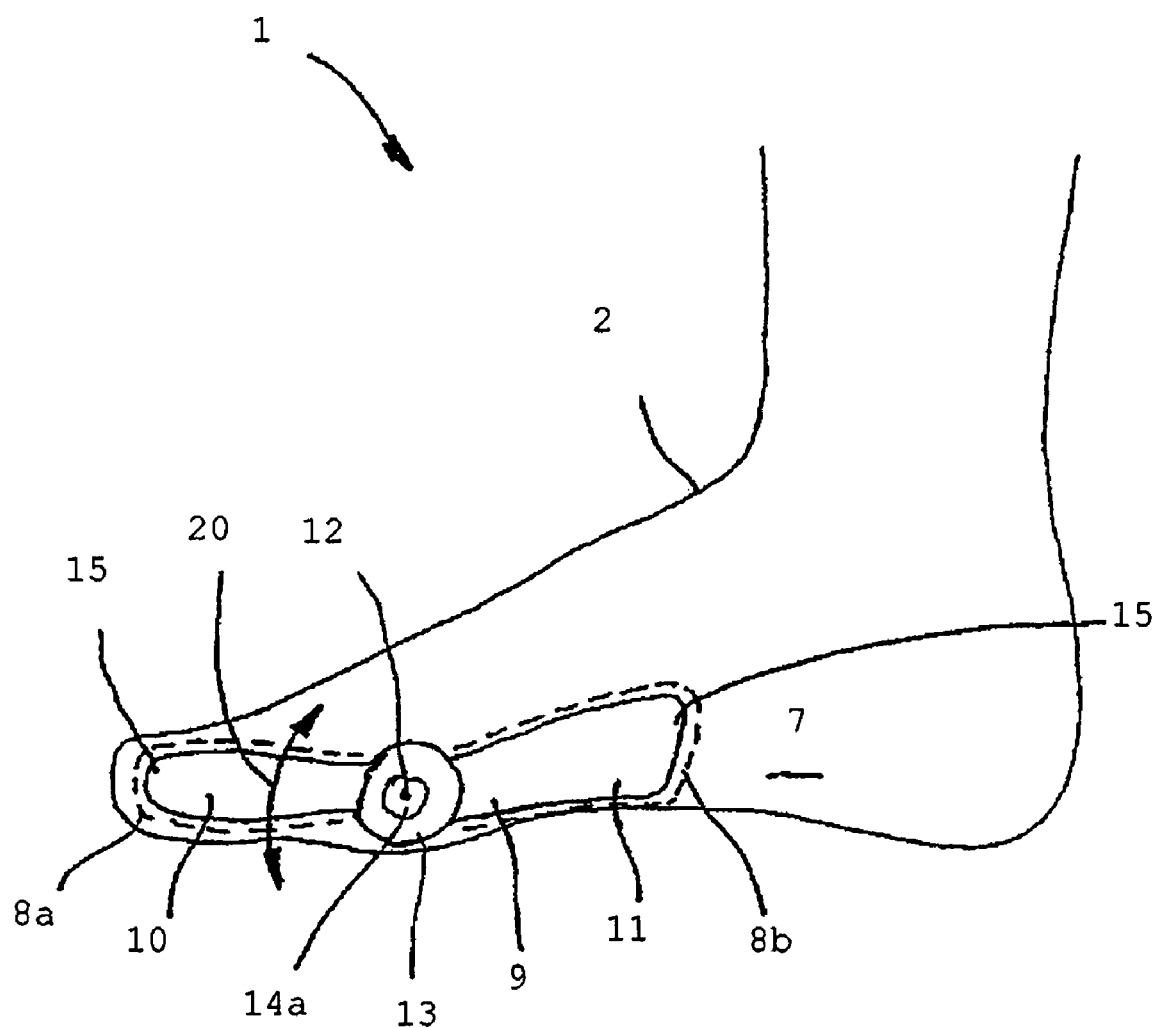
FIG. 2 A diagram of the device according to the invention as in FIG. 1 viewed from the inner side of the foot.
Figure 3:
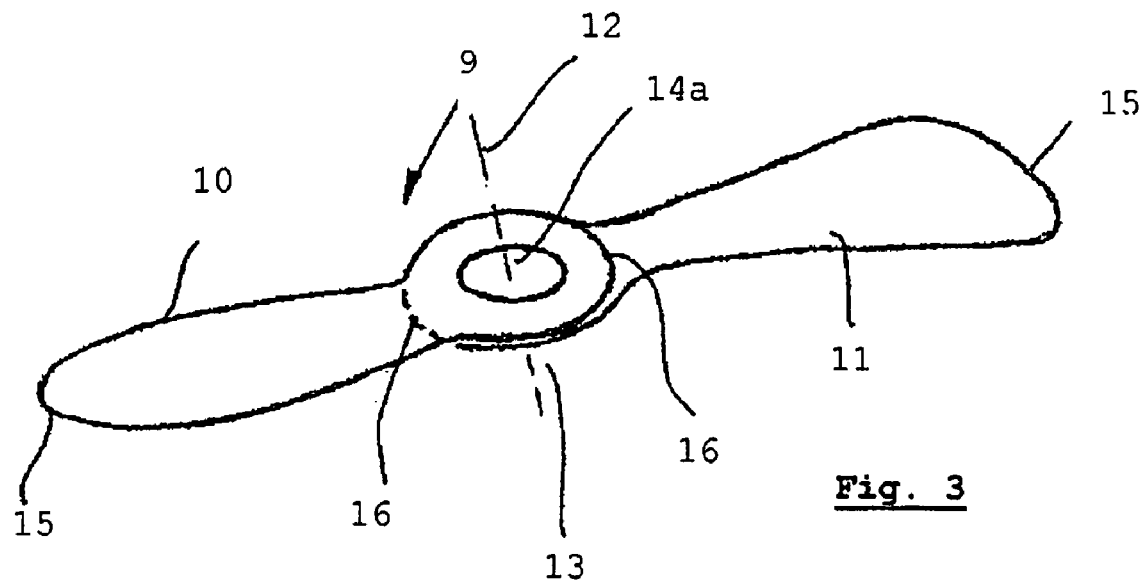
FIG. 3 A diagram of a hinged splint of the device according to the invention shown as a detailed perspective view.
Figure 4:
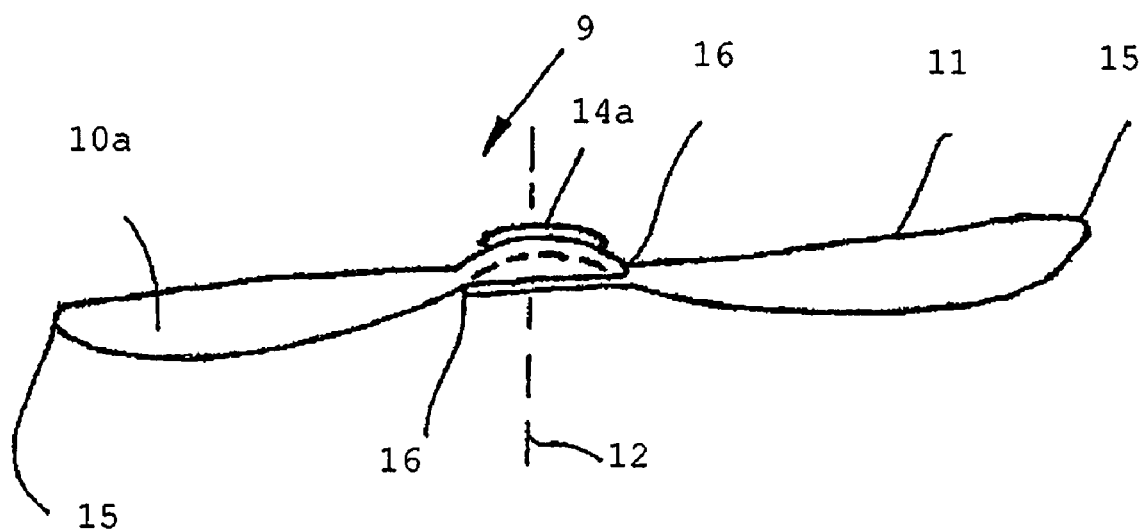
FIG. 4 A diagram of the hinged splint from FIG. 3 as viewed from above.
Figure 5:
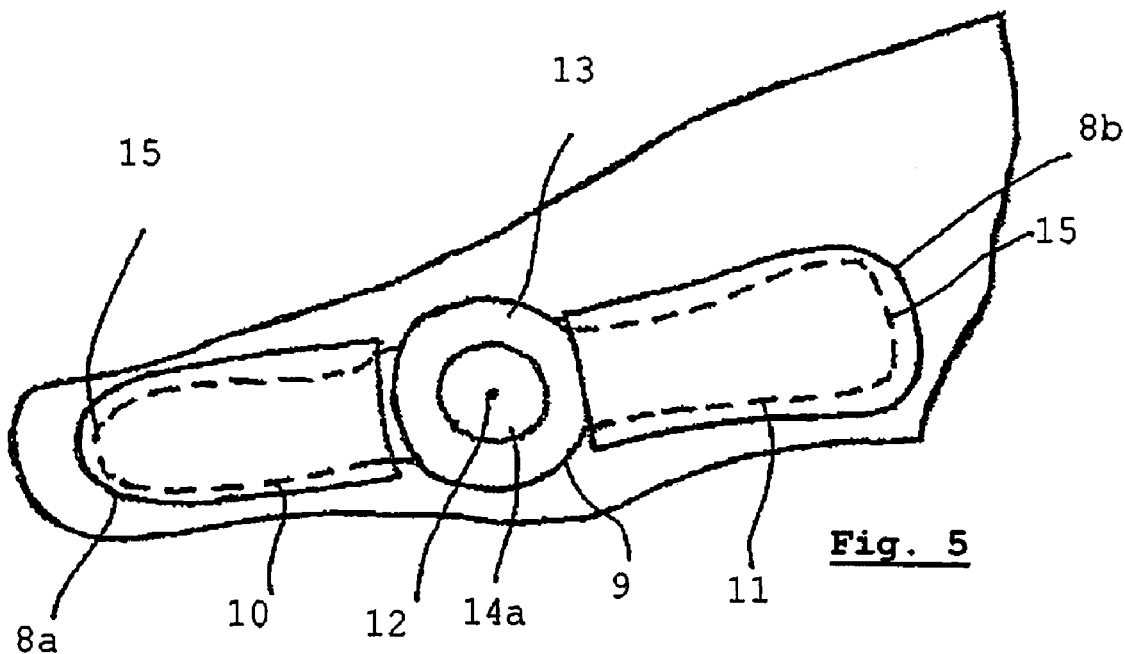
FIG. 5 A diagrammatic sectional view of the front part of the foot (toes and central foot) of a third embodiment of a device according to the invention in an extended position.
Figure 6:
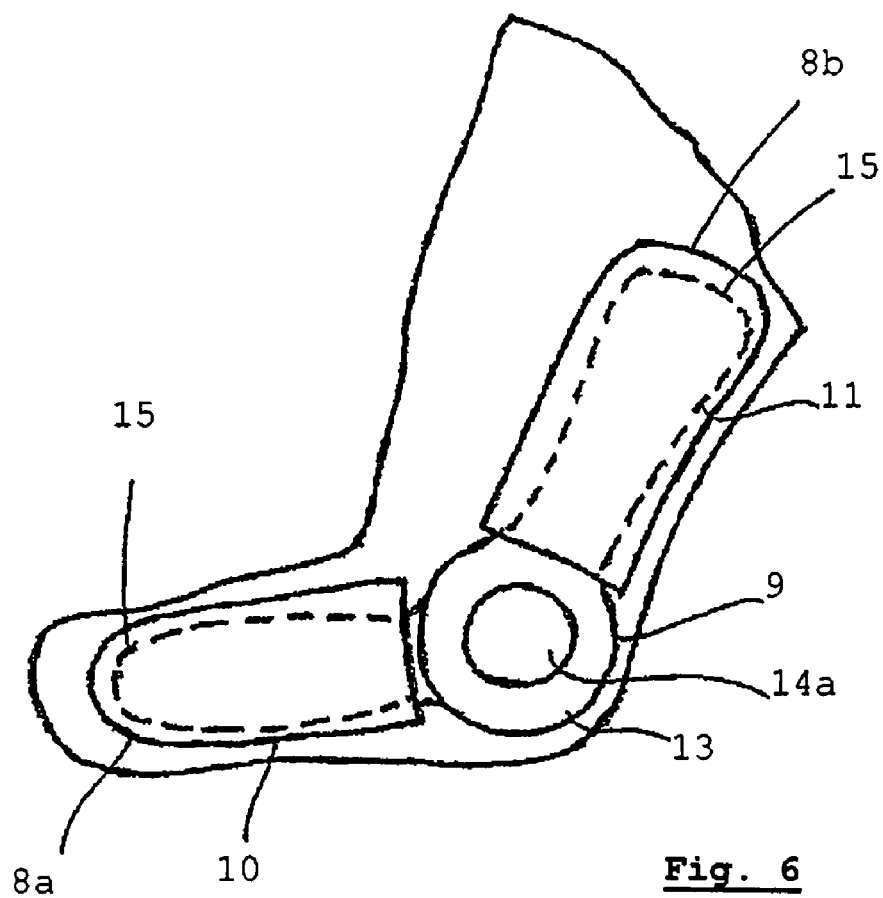
FIG. 6 A diagrammatic sectional view of the front part of a foot (toes and central foot) of the third embodiment of a device according to the invention in a bent position.

In accordance with a third embodiment of the device according to the invention (FIGS. 2, 5, 6) the holders 8a and 8b are formed from pockets that are sewn or attached in a comparable way to the stocking 2. It is helpful with this embodiment for the stocking to be what is known as a compression stocking, so that adequate force transmission to the foot, i.e. an adequately strong transmission of the forces F1 and F3, is ensured, even without the annular bindings 5, 6.

The hinge mechanism 13 is in essence constructed from three parts, the first hinged splint shank 10, the second hinged splint shank 11, and a connecting device 14a for the hinged splint shanks, in particular a tubular rivet. The hinged splint shanks 10, 11 each have a free end 15 and a hinge end 16. The ends at the hinge 16 have a shape approximately that of a universal ball joint, and are designed to correspond to one another in such a way that the hinge ends 16 of the hinged splint shanks 10, 11 can be engaged with one another and interlock.

The hinge mechanism 13 is formed from the hinge ends 16 which take the form of universal ball joints and are connected by the tubular rivet 14a; it is given high stability in the mediolateral direction by the design of the hinge ends 16 having the form of a universal ball joint.

Moreover the bulge in the hinge mechanism 13 has the additional advantage that individual adaptation of the hinge 14a to the patient's foot contour in the region of the main big toe joint is made possible in a simple manner. This is particularly favourable since a round swelling (i.e. what is known as pseudoexostosis) is often found on the foot in the region of the main big toe joint in the presence of the hallux valgus displacement. In a particularly favourable manner, the shape, depth, size and diameter of the concave cap can be individually matched to the patient's foot.

The hinged splint shanks 10, 11, which extend away from the hinge mechanism 13, are favourably shaped in cross-section, or in their full three-dimensional form, to match the contour of the foot. The hinge ends 16 of the hinged splint shanks 10, 11, are not restricted to the shape of a universal ball joint; rather, any three-dimensional shapes that are rotationally symmetrical about the axis 12 and that correspond to one another, in particular the forms of truncated cones or forms with a parabolic cross-section, are suitable.

Metal or plastic are suitable materials for the flexible splint 9 or for the hinged splint shanks 10, 11, and it has been found that a thin, carbon-fibre reinforced plate is particularly favourable, since it can easily be moulded through the application of heat, and demonstrates a high spring force yet with a low material thickness once it has cooled.

The stiffness of the flexible splint 9 in the medio-lateral direction is further increased by a non-constant cross-sectional shape of the shanks 10, 11. This means that a device according to the invention having a flexible splint 9 achieves, on the one hand greater comfort, because the flexible splint 9 can be individually adapted to the patients' foot; on the other hand, an increased spring stiffness in the medio-lateral direction is achieved, with the result, following primarily from this, that a surprising increase in the success of treatment can be achieved.

A device according to the invention 1 also ensures that on the inner side of the foot, or of the big toe requiring correction, only very thin layers of material need to be applied, with the result that the device according to the invention 1 can be worn without significant difficulty in the usual shoe. The freedom of movement of the big toe is in this way also not restricted, since it is possible, using the device according to the invention 1, for the toe to move itself in the natural direction of flexion and extension 20, or for its freedom of movement in this direction not to be restricted (cf. FIGS. 5, 6). This makes this device 1 particularly suitable for long-term treatment, in the day as well as the night, since the patient does not experience any significant hindrance as a result of the device 1.

The cross-sectional form of the hinged splint shanks 10, 11 is not constant. They may, for instance, be bent with constant thickness from flat material, whereby the shaping is adapted to the individual form of the patient's foot. Additionally it is, of course, also possible for the hinged splint shanks 10, 11 to have a lenticular cross-section, in particular a lenticular form such that the material thickness reduces towards the edges of the hinged splint shanks 10, 11, so that the geometrical match of the flexible splint 9 to the patient's foot can be individually further improved.

According to a further embodiment (not illustrated) the orthopaedic device according to the invention 1 for the correction of the faulty positioning of more than one neighbouring toe is further developed for instance through a means of tension being attached to the annular binding 6 around the big toe in the medio-lateral direction, and affecting one or more neighbouring toes which may, for instance, also be surrounded by an annular toe binding. In this way the corrective force of the flexible splint 9 in the medio-lateral direction can be transmitted simply from the big toe to neighbouring toes. Through an appropriate selection of the material thickness for the hinged splint shanks 10, 11, and through suitable selection of the perimeter section of these hinged splint shanks 10, 11, and through the easy adaptability of the spring tension of the flexible splint 9 in the medio-lateral direction, it is possible to affect the spring strength in a simple way and thereby to affect the corrective force F1 for toe position.

Individual adaptation of the corrective force F1 to the specific requirements of the patient is therefore possible with simple means available in any orthopaedic workshop, such as by adapting the perimeter shape of the shanks 10, 11 or changing the cross-section of the shanks 10, 11 and/or the hinge mechanism 13.

A further implementation of the hinged splint 9 of the device according to the invention 1 (FIG. 7) also has a first hinged splint shank 10 and a second hinged splint shank 11 that have an articulated connection via a hinge mechanism 13 and are thus able to pivot around an axis 12. The first hinged splint shank 10 is, when the device 1 is positioned in the region of the patient's big toe, located on the inner side of the foot.

The second hinged splint shank 11 is located in this case in the area of the patient's central foot on the inner side of the foot. The first hinged splint shank 10 has an outer side facing away from the foot 50 and an inner side facing towards the foot 51. The first hinged splint shank 10 has a form that is longitudinally and transversely convex but substantially flat, with a first longitudinal boundary 52 and a second longitudinal boundary 53 as well as a narrow boundary 54. Running next to the longitudinal boundaries 52, 53 the hinged splint shank 10 has slot-shaped openings 55 which form a middle stay 56 and an edge stay 57.

The convexity of the hinged splint shank 10 in its longitudinal and transverse directions are adapted to the anatomical features of a foot.

The annular binding 6, which is attached to the hinged splint shank 10, is provided to fasten the first hinged splint shank 10 to the patient's big toe. The annular binding 6 possesses a loop strap 60 and free ends 61. The loop strap 60 is used to encircle the big toe of the patient. The free ends 61 are passed from the inside of 51 through the slots 55, reaching through them, passing round the edge stay 57, and has a releasable fastening to an outer face of the loop strap 60. This provides secure fastening of the hinged splint shank 10 to the patient's big toe, and permits the size of the loop strap 60 to be adapted to the different sizes of big toes.

The hinge end 16 of the first hinged splint shank 10 features a hinge ring 70, whose central axis is the pivoting axis 12. The hinge ring 70 is favourably joined as one piece with the first hinged splint shank 10.

The hinge ring 70 has an outer side 71, an inner side 72, and an annular step 73 extending from the inner side 72 some way in the direction of the pivoting axis 9.

The second hinged splint shank 11 has an outer face 80 and an inner face 81, as well as a first longitudinal boundary 82 and a second longitudinal boundary 83 together with a narrow end boundary 84. The second hinged splint shank 11 is primarily formed as a flat body with longitudinal and transverse convexity, in which the convexities in the longitudinal and transverse senses are adapted to the anatomical features in the area of the central foot on the inner side of the foot. The material at the free end 15, and at the longitudinal boundaries 82, 83, of the second hinged splint shank 11, like that of the first hinged splint shank 10, is tapered, so that a cross-section, for instance, will show a lenticular shape. Approximately parallel to the longitudinal boundaries 82, 83, the second hinged splint shank 11 has slots 85, so forming a middle stay 86 as well as edge stays 87 and intermediate stays 88 between the edge stays 87 and the central stay 86.

The hinge end 16 of the second hinged splint shank 11 is favourably joined as one piece with the hinged splint shank 11, and takes the form of the hinge disk 90 which, with the hinge ring 70 of the first hinged splint shank 10, forms the hinge mechanism 13. When the device according to the invention is worn by a patient and is attached to the patient+s foot, the hinge disk 90 faces the skin of the foot and lies against it. The hinge ring 70 is positioned on the outside against the hinge disk 90. The hinge disk 90 has, concentric with the annular opening of the hinge ring 70, an annular ridge 91 which extends from the hinge disk 90 some way in the direction of the inner region of the hinge ring 70.

Figure 9:
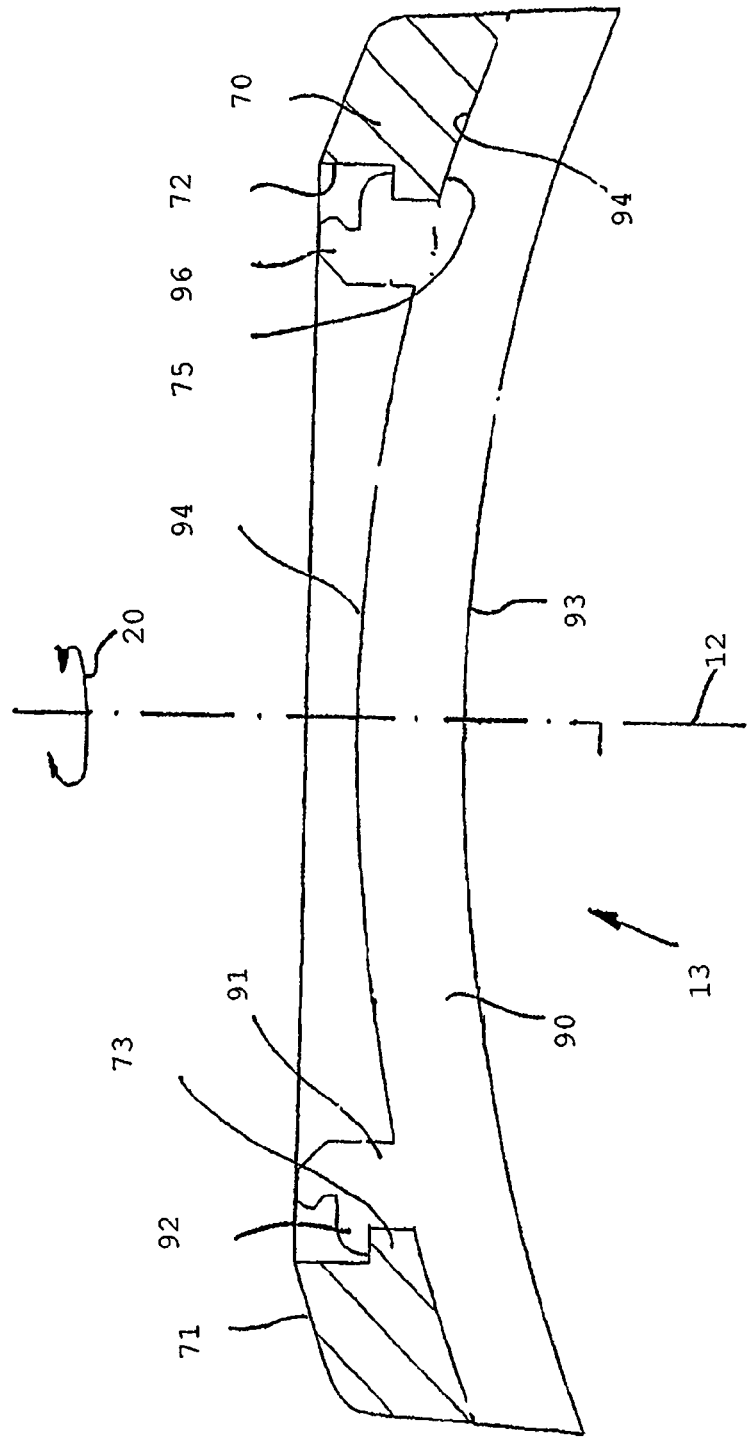
FIG. 9 A transverse section through the hinge mechanism of the hinged splint in accordance with FIG. 7 along the line A-A in FIG. 7.

The annular ridge 91 sits with little or no free play inside the annular step 73 of the hinge ring 70, so that the radial relationship of the hinge disk 90 and of the hinge ring 70 to one another is ensured. For radial localisation of the hinge ring 70 in respect of the hinge disk 90, engaging lug segments 92 are moulded on to the annular ridge 91 (FIG. 9). These function together with an upper face of the annular step 73 so ensuring axial localisation of the hinged splint shanks 10 and 11 to one another. The arrangement of the engaging lug segments 92 will be described in more detail in association with FIG. 9. In order to ensure reliable assembly of the hinge mechanism by pushing the hinge ring 70 onto the hinge disk 90 and engaging the engaging lugs 92 with the annular step 73 it is favourable for the engaging lugs 92 not to extend around the full circumference of the annular step 91, so that the material elasticity of the hinge ring 70 can act as a spring during assembly.

According to a particularly favourable embodiment (FIG. 9) the form of the hinge disk 90 has a concave cross-section, particularly a three-dimensionally concave form, and has a side 93 that faces in towards the foot and an outer side 94 facing the hinge ring 70, which also, corresponding to the inward facing side 93, in particular in the region outside the annular ridge 91, has a concave form or is partially of a concave form. Corresponding to this the hinge ring 70 has an inner side 75 opposite the outer side 71, whose three-dimensional form is such that it lies with its surface against the corresponding inner side 93 of the hinge disk 90 in the area outside the annular step 91.

Figure 8:
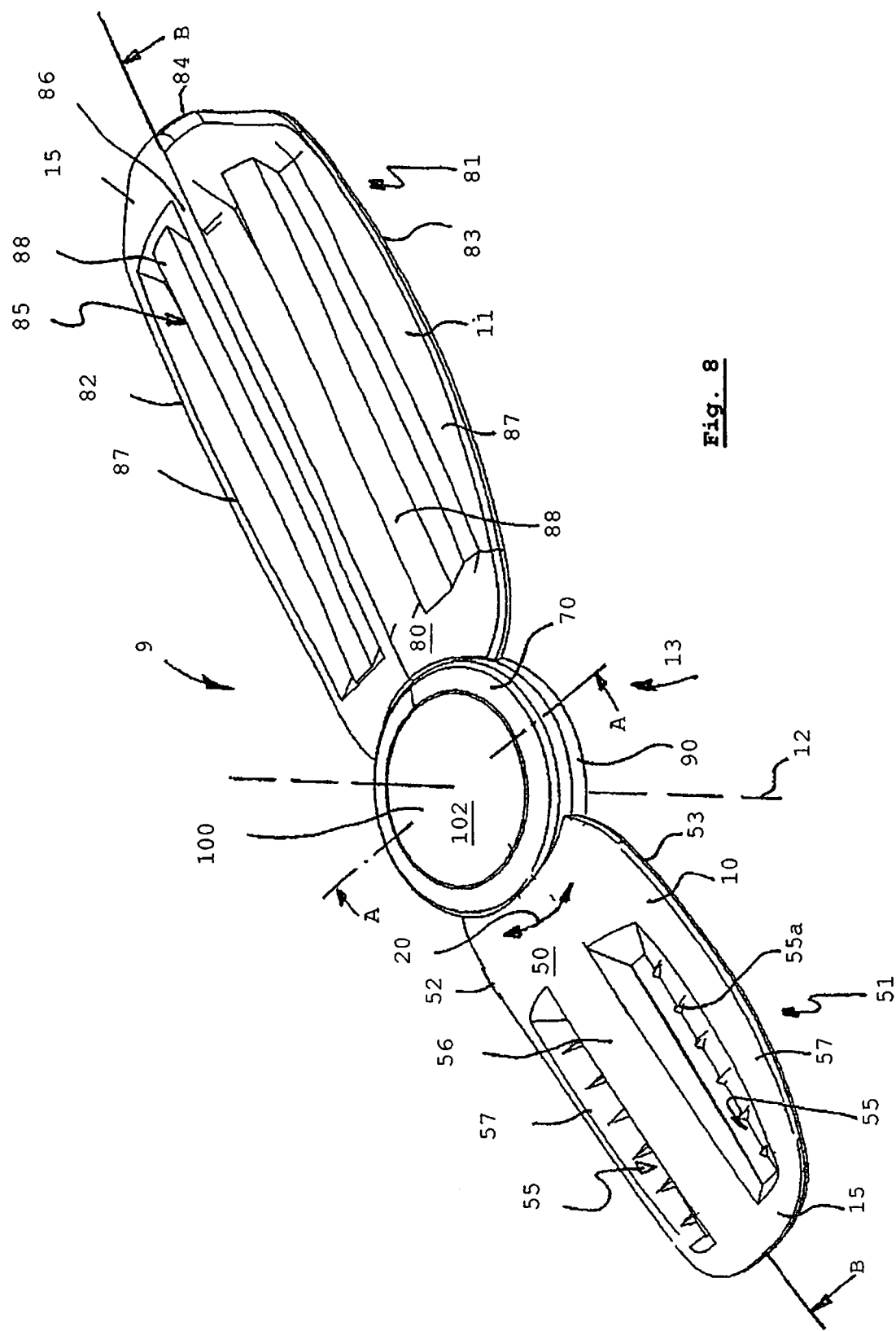
FIG. 8 The hinged splint in accordance with FIG. 7 with a covered hinge mechanism.
Figure 10:
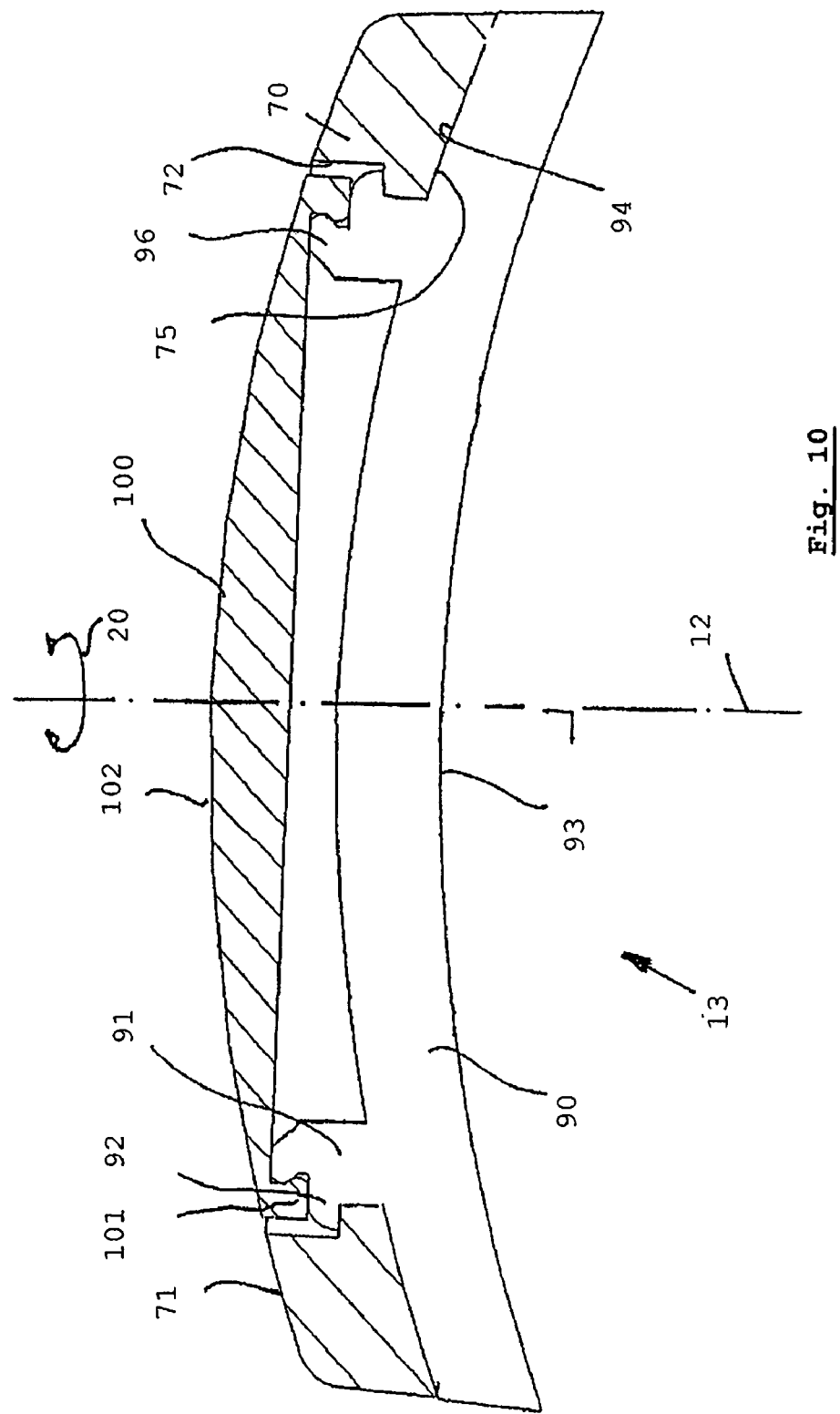
FIG. 10 A transverse section through the hinge mechanism of the hinged splint in accordance with FIG. 8 along the line A-A in FIG. 8.

In addition to the engaging lugs 92, the annular ridge 91 has a further engaging ring 96 or engaging ring segments at its free end, which serve to attach a cap-like closer 100 (compare FIGS. 8, 10).

The closing cap 100 has a means of engagement 101 corresponding to the annular engagement ridge 96, so that the closing cap can be joined to and interlock with the hinge disk 90 or its annular ridge 91. The closing cap 100 has an outer face 102 whose three-dimensional form is shaped such that a harmonious transition from the upper face 73 of the hinge ring 70 is ensured. The closing cap 100 serves to close the open hinge mechanism, and thereby to protect it from soiling and/or damage. Favourably the closing cap 100 is located with some free play against the inner side 72 of the hinge ring, in order to avoid unwanted noise and/or excessive friction.

In this way an easily assembled hinge mechanism 13 is easily created, with an exceptionally high ability to accept bending stress whilst at the same time having low material thickness, and, furthermore, only a small number of components. Additionally, forming the hinge mechanism 13 as an annular hinge means that high bending forces and bending moments can be introduced to the hinge mechanism 13 without impairing its ease of movement or generating excessive wear. This is primarily due to the large supporting width which is made possible by engagement of the lugs 92 on the outside with an annular step 72 on the inside of the hinge ring 70.

This means that the hinged splint 9 primarily consists of just two individual parts which provide the function of the splint 9. The closing cap 100 merely has a sealing function, and is not necessary for creation of the hinge.

A particular advantage of forming the hinge ring 13 in this way is that in the region of the main big toe joint where a pseudoexostosis might be present on the patient's foot, the contacting inner side 93 of the hinge disk 90 has a smooth surface, i.e. has no protruding or prominent parts or edges, and this considerably improves comfort. The concave shape takes the maximum possible pressure off sensitive regions of the foot (pseudoexostosis), thus minimising any pain the patient may feel, since the compressive force $F_2$ is distributed over a wide area. Along the length (FIG. 11) of the hinged splint 9 care is taken to see that the inner face 51, the inner face 93, and the inner face 81 of the hinged splint components 10, 11, present a continuous, step-free, smooth curve, which further improves the wearer's comfort. The slots 55 and 85 may have teeth 55a on their side faces which provide grip to prevent the annular bindings 6 that are to be threaded through them from slipping.

Figure 11:
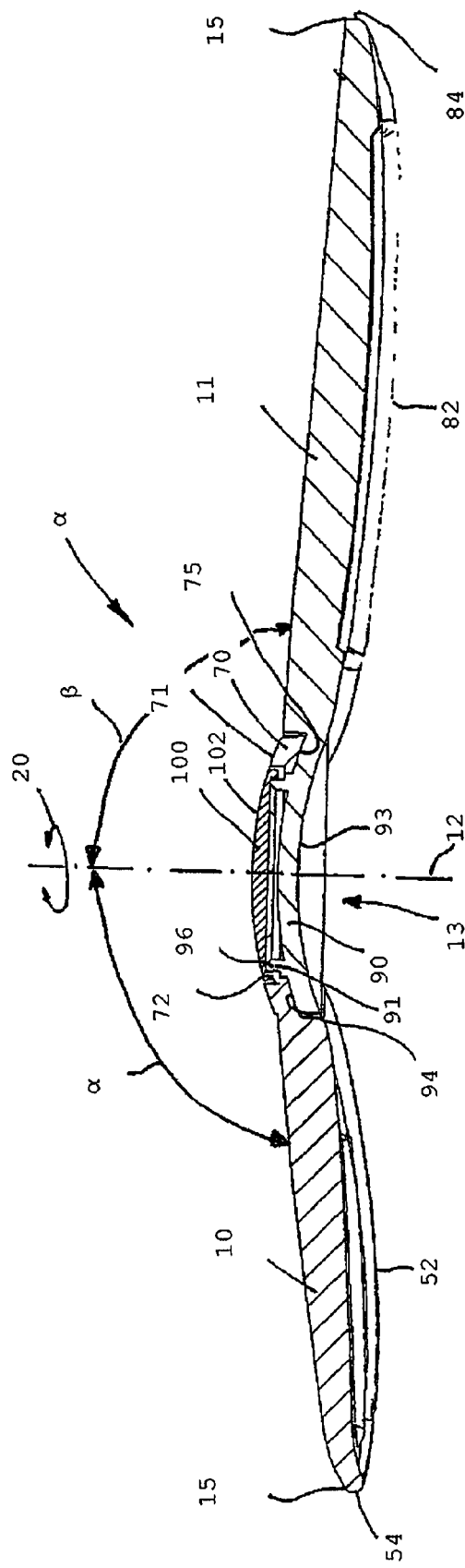
FIG. 11 A longitudinal section through the hinged splint in accordance with FIG. 8 along the line B-B in FIG. 8.

The hinged splint shanks 10 and 11 enclose angles $\alpha$ and $\beta$ respectively between their length and the pivoting axis 12 (compare FIG. 11). The angles $\alpha$ and $\beta$ are chosen so that the hinged splint 9 can be placed against a patient's foot in such a way that the pivoting axis 12 aligns approximately with the anatomical joint axis of the main big toe joint, so that when the hinge pivots with the hinged splint shanks 10 and 11 attached to the foot, a kinetic pivoting movement of the hinged splint 9 largely matching the anatomical conditions of the big toe joint is permitted. The angles $\alpha$ and $\beta$ are also chosen in such a way that correction in a direction towards an orthopaedically proper position can be achieved for a big toe positioned at an angle toward the outer side of the foot (hallux valgus positioning).

It is of course also within the scope of the invention to select the angles $\alpha$ and $\beta$ in such a way that it is also possible to correct the less frequently occurring hallux-varus position, i.e. an incorrect positioning of the toe in which it is shifted towards the inner side of the foot away from the normal position. Selection of the angles $\alpha$ and $\beta$ in accordance with the criteria mentioned above is, of course, possible for all the embodiments outlined in this application, and is not restricted to the embodiments according to FIGS. 7 to 11. Depending on the severity of the incorrect toe positioning and the desired correction force, values in the range between 75° and 115° have been found effective for angle $\alpha$. Within this range, a high proportion of the hallux valgus and hallux varus displacements found are correctable. In extreme individual cases, it is of course also possible for an angle $\alpha$ outside this range to be necessary. For the angle $\beta$ an angle of approximately 70° to 110° has been found effective in order to correct a high proportion of the typically occurring hallux valgus and/or hallux varus displacements. It is, of course, also true for the angle $\beta$ that in special cases a larger or smaller value may be selected.

Figure 7:
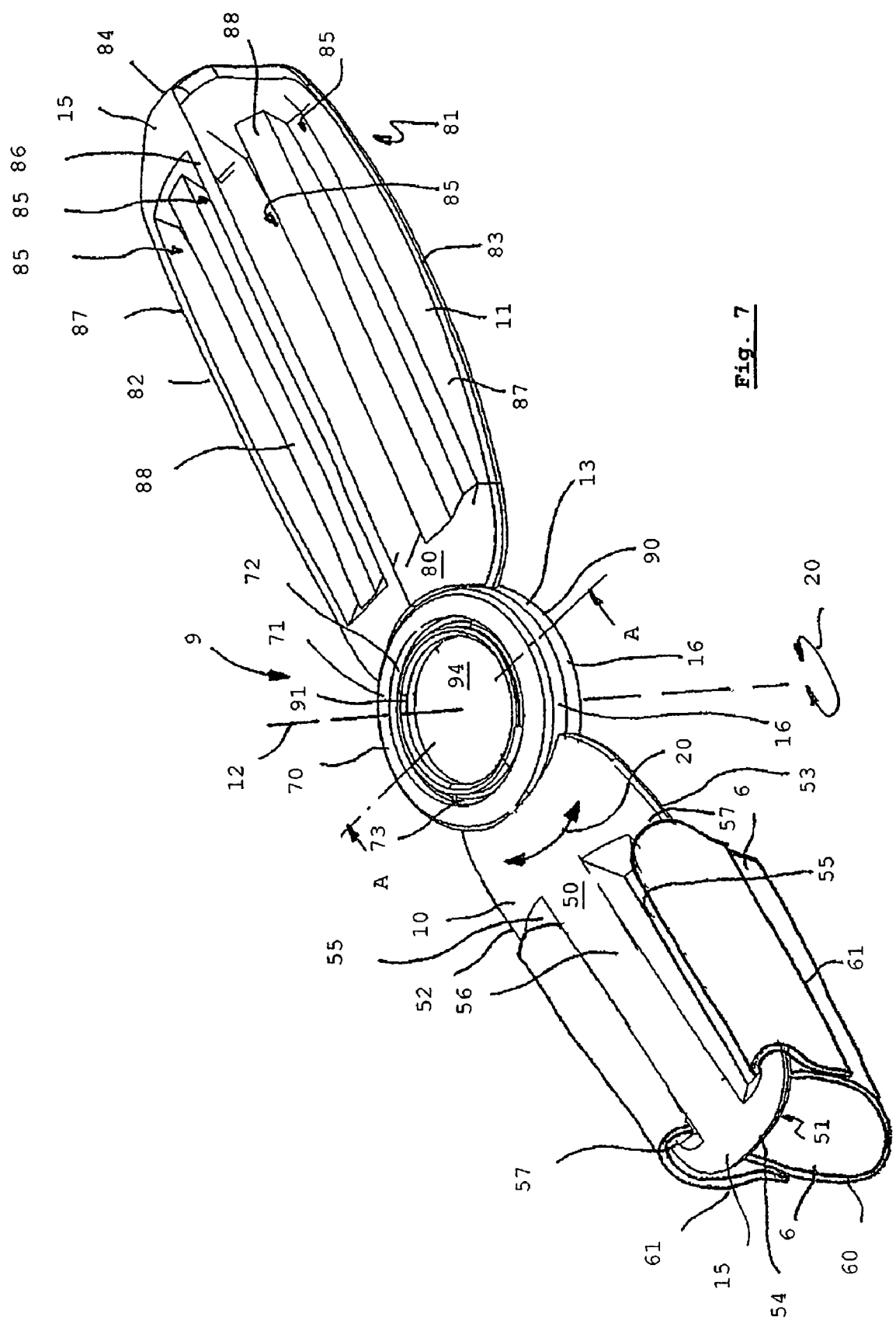
FIG. 7 A perspective view of a further embodiment of the hinged splint of the device according to the invention.

A further embodiment of the hinged splint 9 of the device according to the invention 1 (FIG. 12) is substantially identical in structure to the embodiment in accordance with FIG. 7, and is based on the same principle for the correction of displaced toes. The difference between the embodiments in accordance with FIGS. 7 to 11 and the embodiment in accordance with FIGS. 12 to 17 is merely the hinge mechanism 13, which has a somewhat different design. The inner face 72 of the hinge ring 70 extends somewhat further in the axial direction. Additionally, the annular ridge 91 of the hinge disk 90 only has the engaging lug segments 92, but not the engaging lug segments 96 mounted on top for holding the closing cap 100.

The closing cap 100 (compare FIG. 13) is inserted into the hinge ring 70 in such a way that an external ring wall 105 of the closing cap 100 operates in combination with the inner side 72 of the hinge ring 70 in such a way that the closing cap 100 is fastened to the hinge ring 70 by means of a press fit or of an adhesive seating. In this construction it is advantageous if the closing cap 100 does not move relative to the hinge ring 70, so that any abrasive effect against a stocking which may enclose the hinged splint including the hinge device 16, or with the inside of the shoe, is minimised. This ensures that, between the partial regions 50, 102, 80 of the outer face of the hinged splint 9, no relative movement of the surface sections 80, 100, 70 in the region of the hinge mechanism occurs when the hinged splint is operated. A further difference is that the sliding hinge surfaces 94 of the hinge disk 90 and the corresponding surface 75 of the hinge ring 70 are formed from planar ring surfaces; this represents a simpler construction, with the effect that the radial guidance of the hinge ring 70 relative to the hinge disk 90 takes place exclusively through an outer face 91a of the annular ridge 91 and an inner face 73a of the annular step 73.

It is, of course, also within the scope of the invention to implement the closing cap 100, according to the embodiment shown in FIGS. 12 to 17, on an embodiment of the hinge mechanism 13 according to FIGS. 7 to 12. The same applies to the design of the sliding surfaces 75, 94 with respect to the implementing the principle according to FIGS. 7 to 12 to a hinge mechanism 13 according to FIGS. 13 to 17.

Figure 12:
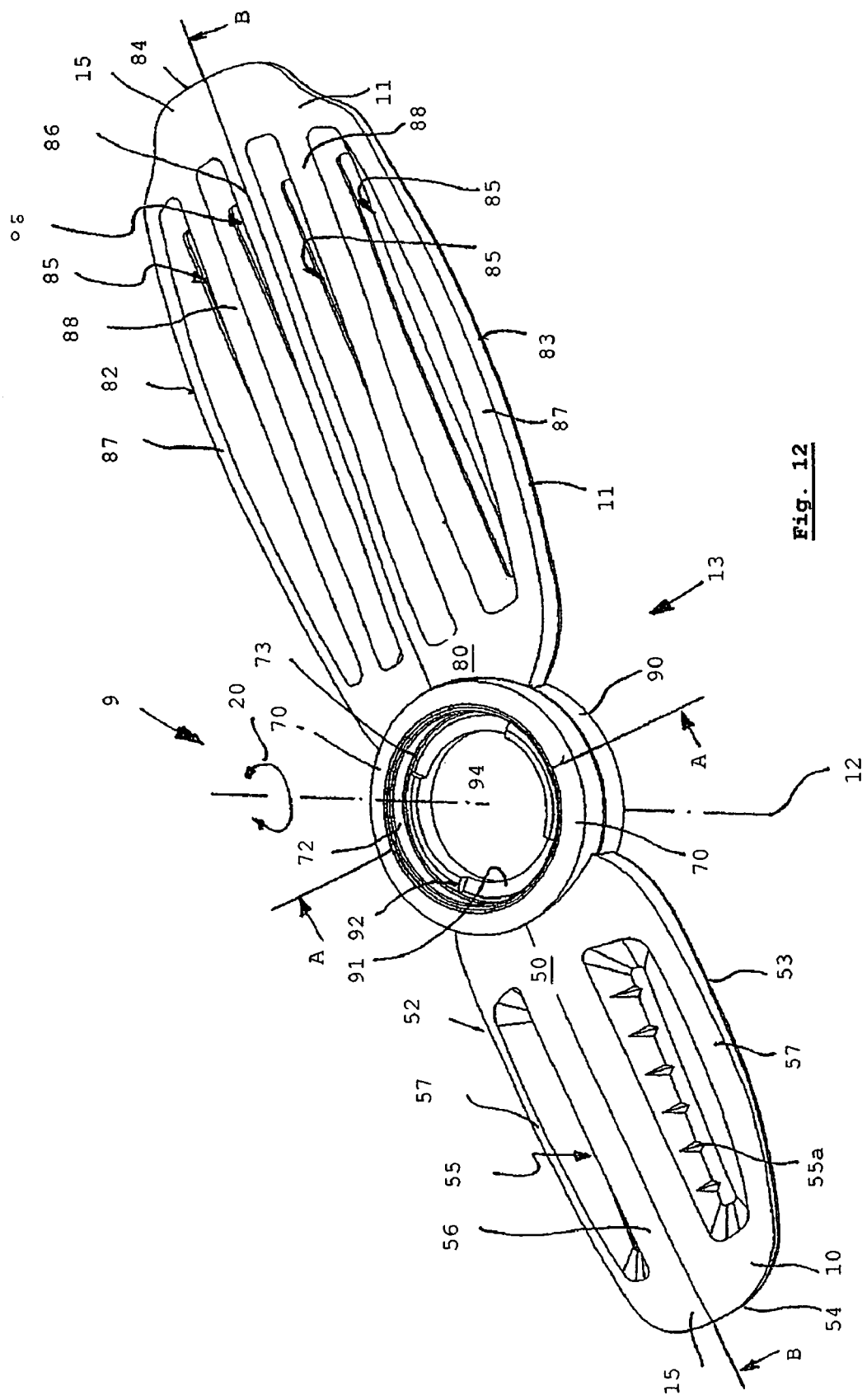
FIG. 12 A perspective illustration of a further embodiment of the hinged splint of the device according to the invention.
Figure 13:
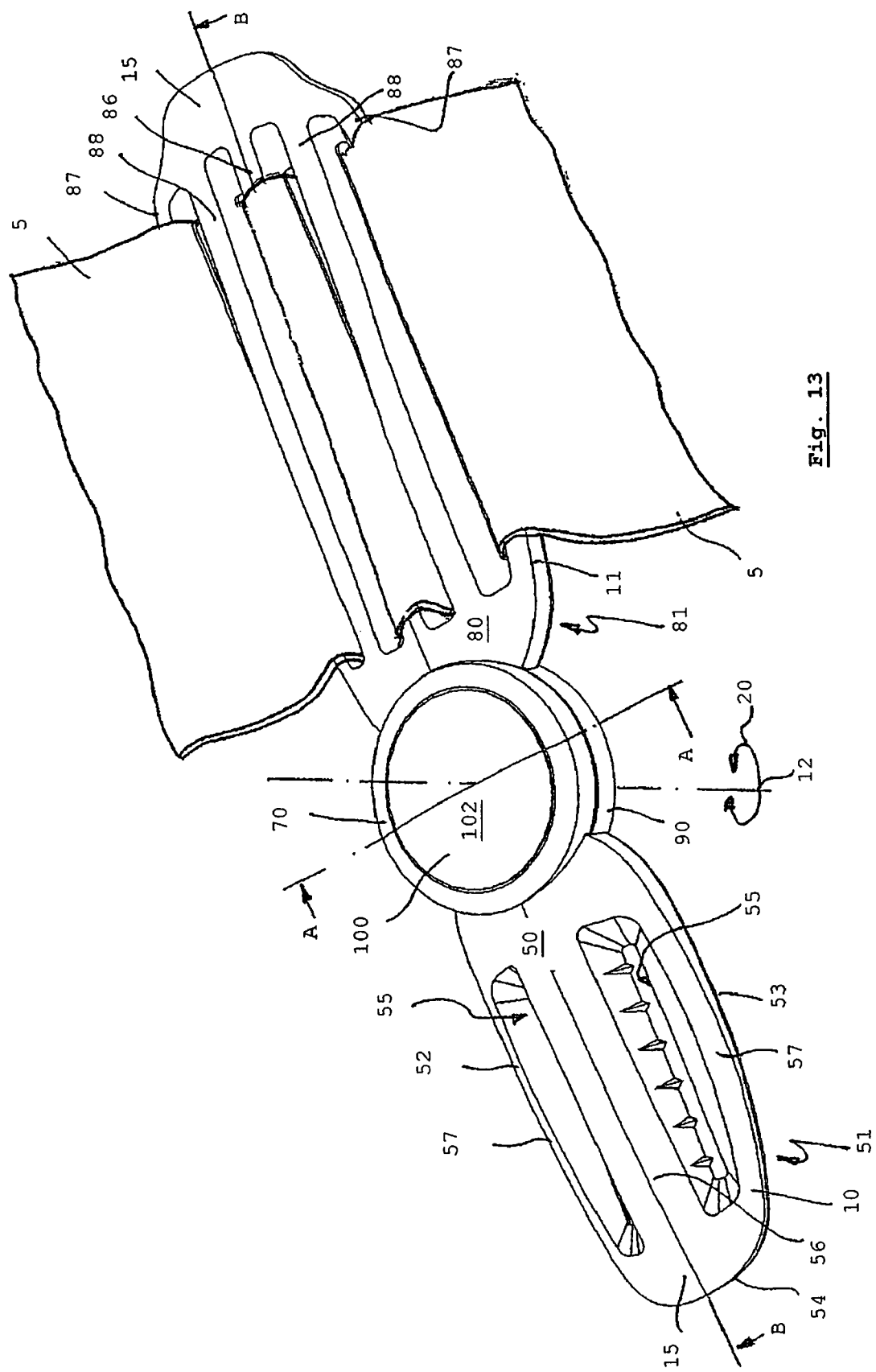
FIG. 13 A perspective illustration of the hinged splint in accordance with FIG. 12 with a covered hinge mechanism.
Figure 14:
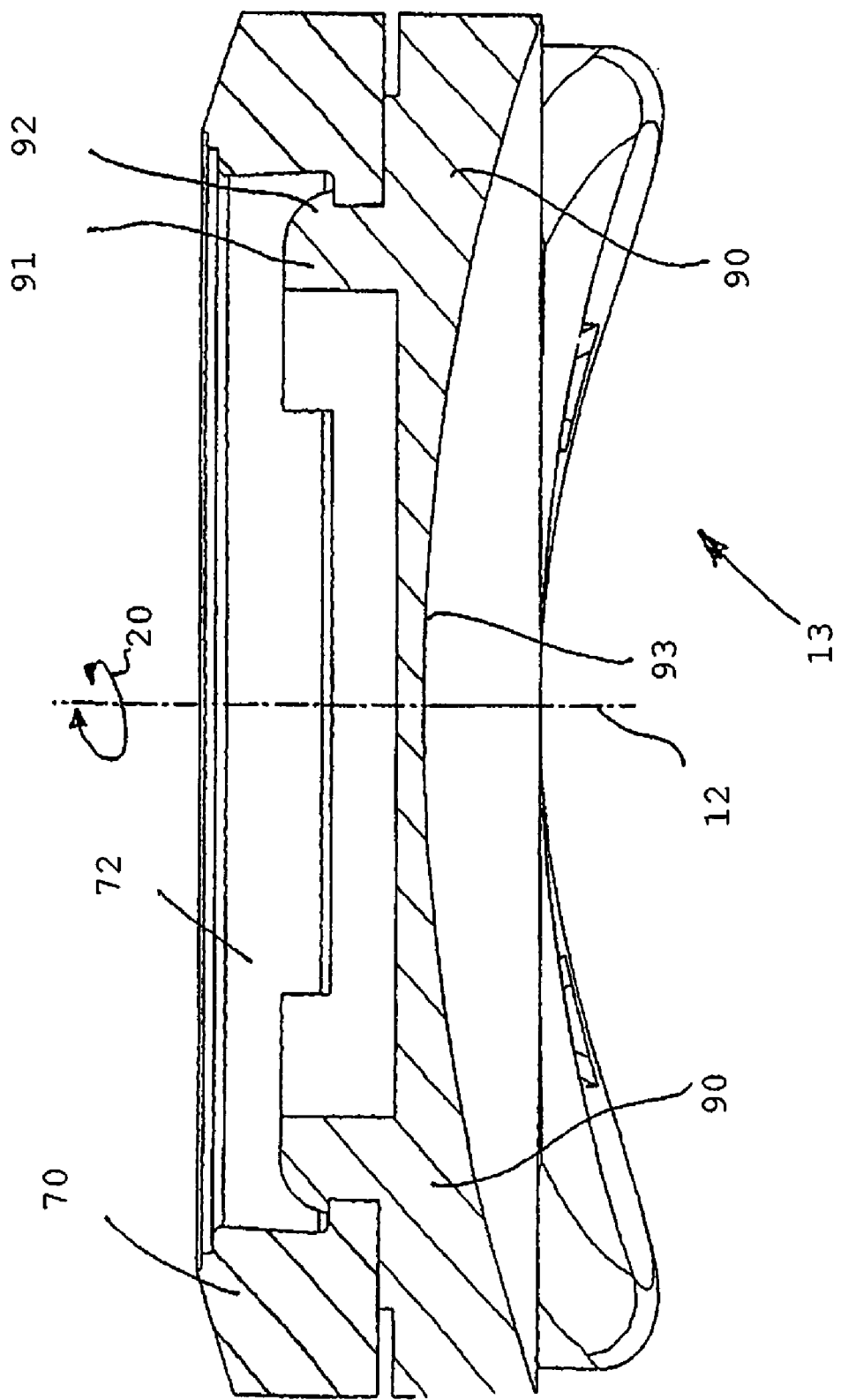
FIG. 14 A transverse section through the hinge mechanism of the hinged splint in accordance with FIG. 12 along the line A-A.
Figure 15:
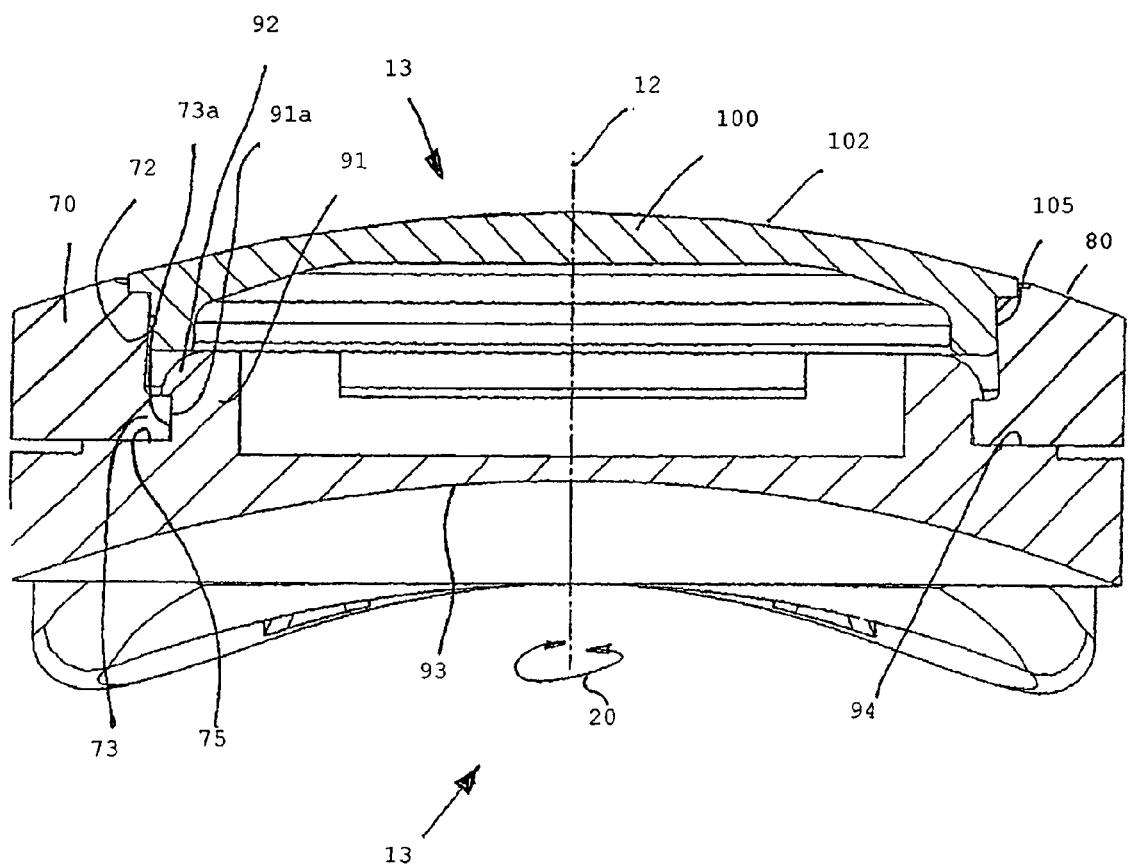
FIG. 15 A transverse section through the hinge mechanism of the hinged splint in accordance with FIG. 13 along the line A-A.
Figure 16:
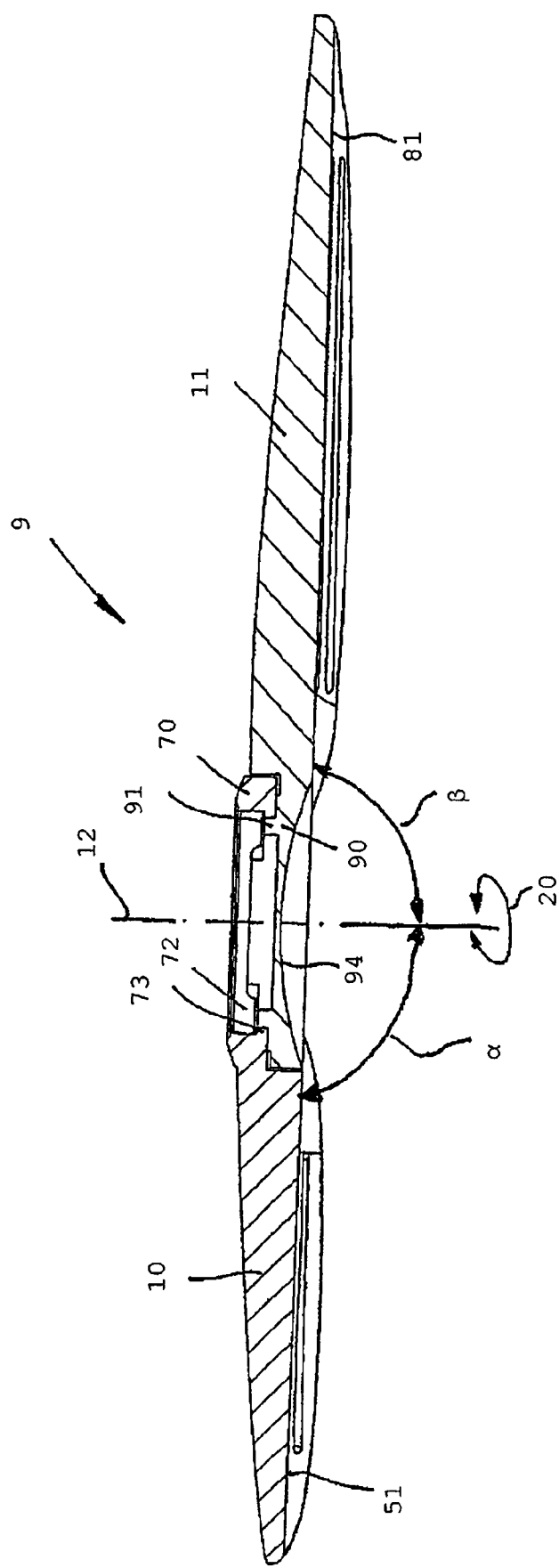
FIG. 16 A longitudinal section through the hinged splint in accordance with FIG. 12 along the line B-B.

It can be seen from a longitudinal section of the embodiment in accordance with FIGS. 12 and 13 (FIG. 16), that the effective correction angle β between the pivoting axis 12 and the effective regions of the hinged splint 9 lying against the foot is 90°.

Further, the hinged splint shanks 10 and 11 have a straight three-dimensional form in their effective length along their sides 51 and 81, which is not particularly closely adapted to the anatomical curve of the foot or of the big toe. Thus this kind of embodiment of the hinged splint represents a simplified form of the hinged splint 9 which is nevertheless effective for a large number of the cases requiring treatment. The corresponding angles α and β in FIG. 11 are shown, for the sake of simplicity, between the pivot axis 12 and the outline, which does not however make a great difference. What is meant in any case is the effective angle between a conceptual effective axis of the hinged splint shank and the pivot axis 12, whereby inserting such an effective axis on the drawing in the case of an entirely free-form hinged splint adapted to the anatomical features of the human foot in accordance with FIG. 11 can only be a rough estimate. It is therefore clear that the angles α and β in accordance with FIG. 16 and the angles α and β in accordance with FIG. 11 are in principle the same effective angles.

Figure 17:
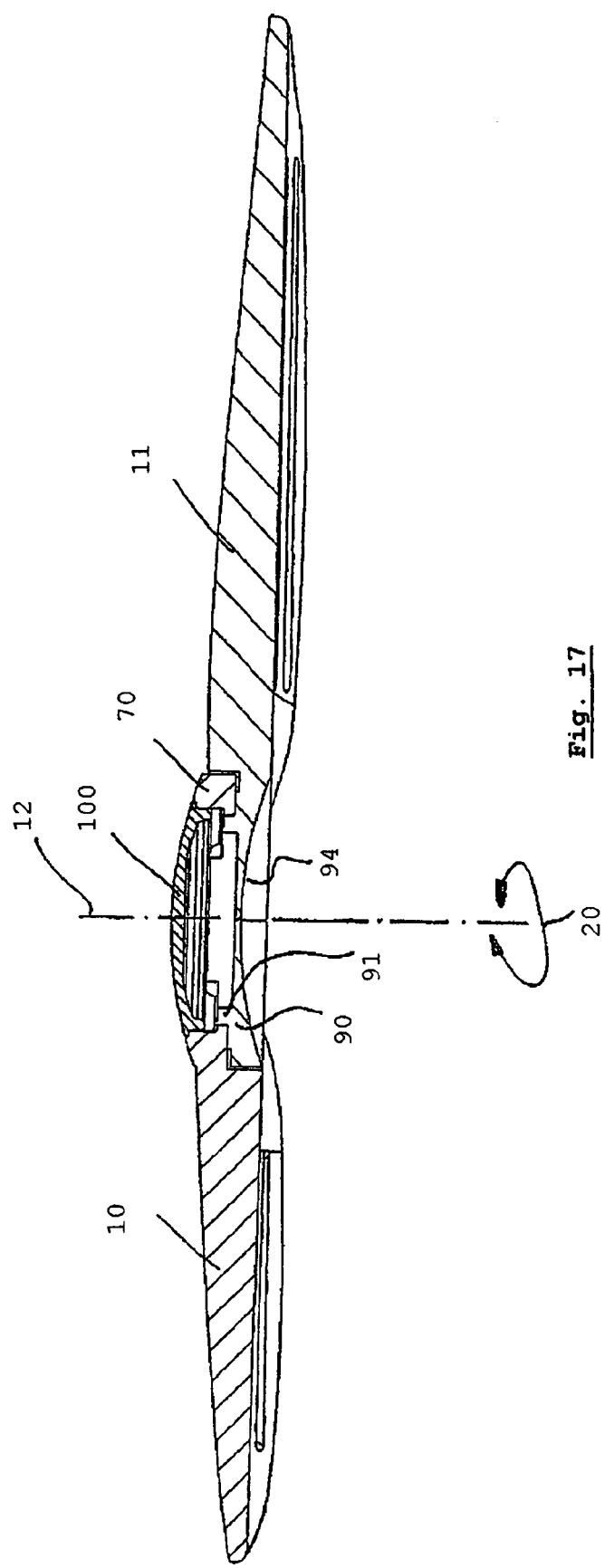
FIG. 17 A longitudinal section through the hinged splint in accordance with FIG. 13 along the line B-B.

In the longitudinal section representation according to FIG. 17, the embodiment of the hinged splint 9 in accordance with FIGS. 12 and 13 is illustrated with a closing cap 100 applied.

Figure 18:
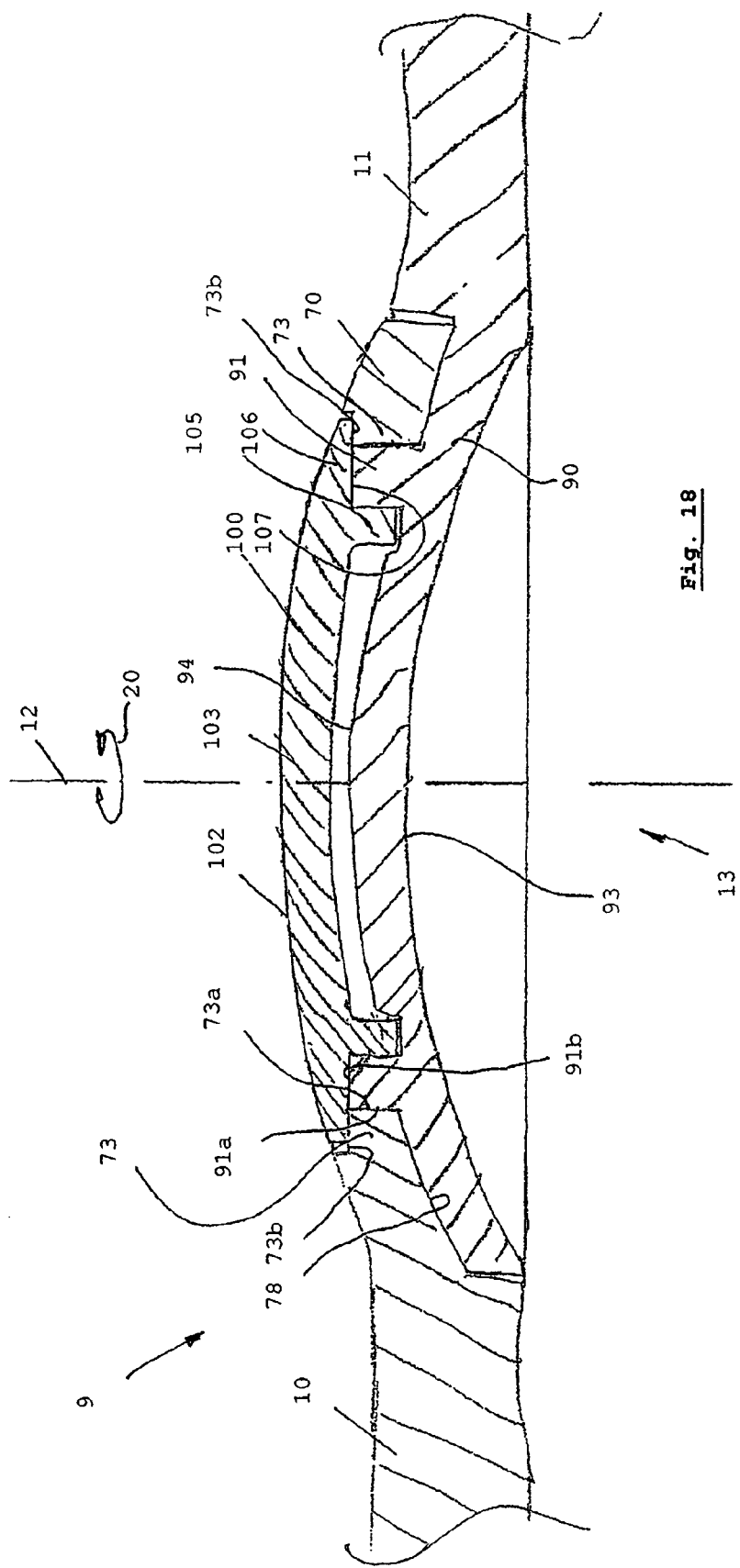
FIG. 18 A further embodiment of the hinge of the hinged splint shown in a partial longitudinal section.

A further embodiment of the hinge mechanism 13 (FIG. 18) of the hinged splint 9 of the device according to the invention 1 is also constructed as what is called a sliding annular hinge with a hinge disk 90 and a hinge ring 70. The hinge ring 90 has an inner side 93 facing the skin of the foot and, opposite this, an outer side 94. From the outer face 94, an annular ridge 91, which has an outer annular ridge surface 91a, extends some way in a direction away from the patient's foot.

The outer annular ridge surface 91a serves to guide the hinge ring 70 radially, and operates with little or no play together with the inner hinge ring face 73a.

The hinge disk 90 is, as in the foregoing embodiment, favourably concave in shape, in particular having a three-dimensionally concave form, and has, outside the annular ridge 91, a partial region of the outer side 94 which serves as a sliding hinge surface and which operates together with a corresponding sliding hinge surface 78 of the hinge ring 70. The sliding hinge surfaces are concave in shape. In the embodiment according to FIG. 18 the height of the annular step 73 of the hinge ring 70 is selected in such a way that one upper surface 73b of the annular step is flush with an upper surface 91b of the annular ridge 91, or protrudes somewhat beyond it. In this way the interaction of the annular ridge 91 and the hinge ring 70 with surfaces 91a and 73a ensures radial guidance of the hinged splint shanks 10, 11. The axial guidance of the hinged splint shanks 10, 11 with respect to one another is ensured in one direction by the sliding surface 78 and its corresponding sliding surface section on the outside 94 of the hinge disk 90. In the direction opposite to this direction, the axial positioning of the hinged splint shanks 10, 11, or of the hinge ring relative to the hinge disk 90 is provided as explained below.

The closing cap 100 is, in addition to its function of closing the hinge mechanism 13, also formed as an axial bearing. The closing cap 100 has a closing cap body 103, which, as in the embodiments described above, substantially covers the hinge mechanism 13, thereby protecting it from soiling. From the closing cap body 103 an annular ridge 105 extends opposite to the upper side 102, whose diameter is chosen such that it can be inserted inside the annular ridge 91 of the hinge disk 90 in the space surrounded by the annular ridge 91.

Outside the annular ridge 105 the closing cap 100 is surrounded by a projection 106 whose radial dimension is such that it protrudes to some extent beyond the annular ridge 91 and lies on the upper side of the annular step 73b with little or no axial play. In this way, an underside 107 of the annular projection 106, which operates together with the upper side 73b of the annular step 73, serves as an axial abutment. In order for such a hinge construction to be able to accept the high bending forces that the hinged splint 9 must generate, without damage and over long periods, the closing cap 100 is advantageously glued or otherwise securely fastened to the hinge disk or to its annular ridge 91 at one or more of their contact surfaces.

This hinge mechanism 9 also has the special advantage that the surfaces 93 that lie against particularly sensitive regions of the foot, e.g. in the region of a pseudoexostosis, are flat, i.e. there are neither projections nor hollows that could irritate those regions of the skin. Furthermore the hinge design according to FIG. 18 has a particularly high bending stiffness, and does not easily come apart even if the splint is excessively bent. This means that if improperly handled by patients e.g. by being twisted, excessively bent or similarly treated, the two hinged splint shanks 10, 11 will not come apart.

Plastic, in particular plastic that is impact-resistant and non-irritating to the skin, e.g. of the polycarbonate class, has been found to be favourable material for the hinged splints.

Figure 19:
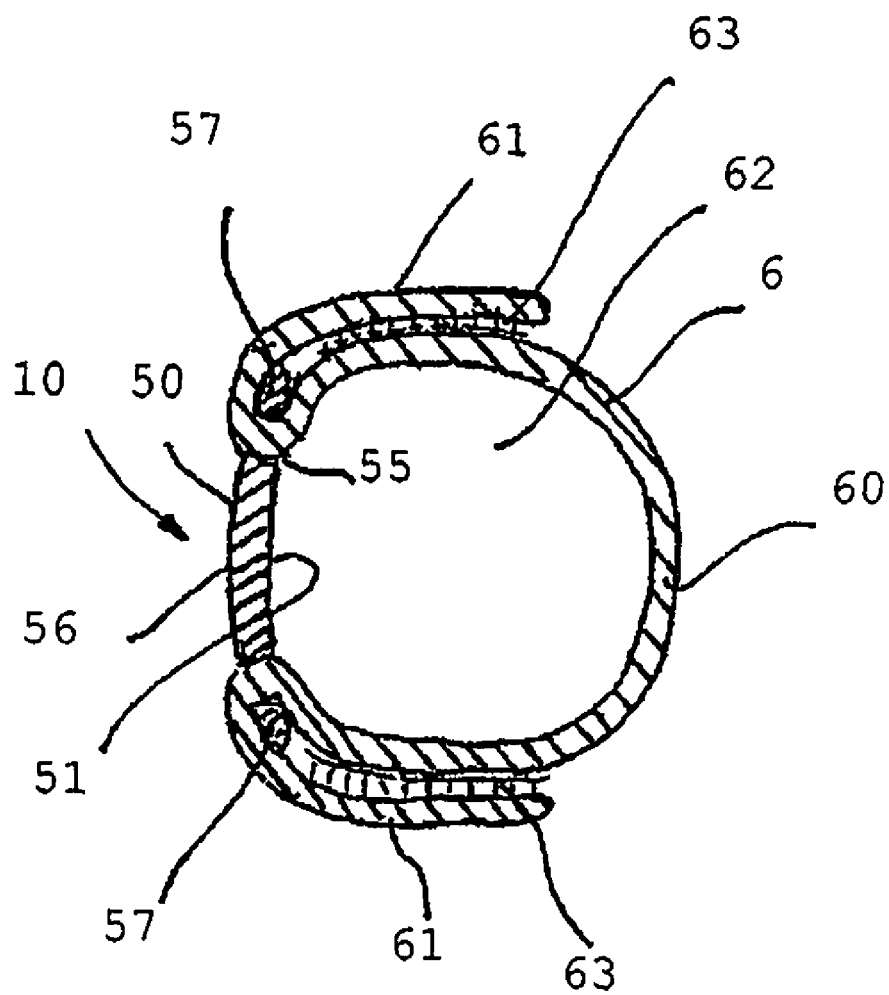
FIG. 19 A cross-section through the shank of a hinged splint and the annular binding that belongs to it in the region of the big toe.
Figure 20:
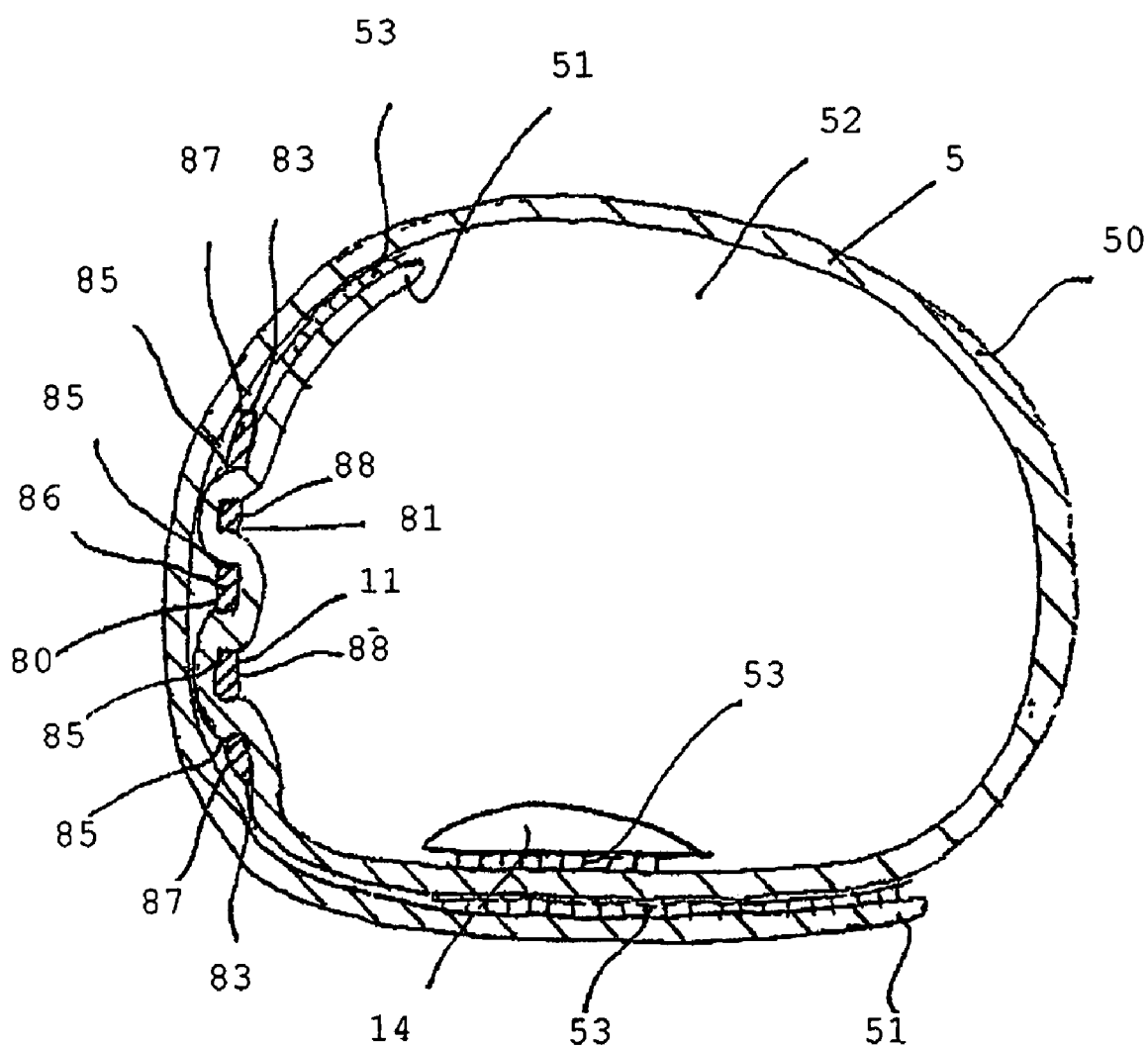
FIG. 20 A cross-section through the shank of a hinged splint and an annular binding according to the invention in the region of the central foot.

The fastening of the hinged splint 9 to the patient's foot and the routing or threading of the annular bindings 5, 6 through the slots 55, 85 of the hinged splint 9 are described in more detail below with the aid of FIGS. 19 to 21.

The annular binding 6 in the region of the big toe (FIG. 19) serves as a fastening mechanism, and has both a loop strap 60 and free ends 61. The loop strap 60 together with the first hinged splint shank 10 encloses an inner region 62 where the patient's toe is located. The free ends 61 are passed from the inside 51 through the slots 55 and round the edge stay 57, enclosing it. As a result, the free end 61 of the annular binding 6 is positioned close to the hinged splint shank 10 on the outside with the loop strap 60. The free end 61 is favourably attached with a velcro fastener 63 to the outside of the loop strap so that it can easily be detached. This type of fastening of the free end 61 can be applied to both free ends 61 of the annular binding 6. Nevertheless, in some cases it is also favourable for one free end 61 to be passed around one edge stay 57 and, if appropriate, sewn permanently to the loop strap 60, and for only one other free end 61 to be joined with a velcro fastener or similar, comparable easily-released surface fastening to the loop strap 60.

The annular binding 5 serves as a fastening mechanism and as a binding to support and realign the transverse arch of the foot, and is also be joined with the second hinged splint shank 11 forming a loop strap 50. The annular binding 5 also has free ends 51. One free end 51 is passed from the inside 81 through the first slot 85 close to the underside of the foot, lying on the outside of the first intermediate stay 88, passing through the second slot 85 from the outside 80, lying on the inside 81 in the region of the middle stay 86 and passing through the next slot 85 from the inside 81 through to the outside, lying on the second intermediate stay 88 on the outside and passing through the last slot 85 from the outside 80 to the inside.

The remaining free end 51 is positioned, for example, against the instep of the foot. The remaining part of the annular binding 5, which is not involved in threading through the second hinged splint shank 11, is passed around the patient's foot to the underside of the foot and the top of the foot, overlaps the second hinged splint shank 11 in the region of the slots 85, and is fastened to the second free end 51 on the outside of the loop strap 50. Velcro fasteners, in particular hook fasteners or mushroom velcro fasteners 53, have been found effective as a means of fastening. In this method of threading the annular binding 5 through the second hinged splint shank 11 and then wrapping around the entire central foot is particularly advantageous, since the edge boundaries 83 of the hinged splint shank 11 do not lie directly against the skin of the foot, thus avoiding the formation of pressure points.

In certain cases it can also be favourable for the two centrally positioned slots 85 to be omitted, and for the annular binding 5 simply to be passed through the outermost slots 85 without taking the path around the middle stay 86. This embodiment has the advantage that in the region of the hinged splint shank 11, inasmuch as this lies against the foot, there are fewer level variations and therefore fewer pressure points on the foot. In the region of the internal space 52 surrounded by the loop strap 50, in which the central foot region of the patient is located, it is advantageous to attach the pad 14 to the annular binding 5 also using Velcro fasteners 53 in the area of the underside of the patient's foot.

A further advantage of this method of threading the annular binding 5 is that it is not necessary to thread through the openings 85 of the hinged splint shank 11 in order to apply the splint 9, but merely for the ready-threaded annular binding to be placed around the foot and to be firmly tied and fastened underneath the foot. This makes it possible to easily adjust or readjust the tightness of the annular binding 5, and thereby its corrective effect on the transverse arch of the patient's foot in the region of the central foot.

A further embodiment of the threading of the annular binding 5 through the second hinged splint shank 11 (according to FIG. 5), is carried out by passing a first free end through a slot 85 from the inside 81 and around the edge stay 87 in the region of the underside of the foot, and for it to be joined on the outside to the loop strap in the region of the underside of the foot by means of connecting elements 53. The other free end 51 is passed in the region of the top of the foot from the inside 81 through a slot 85 at the edge to the outside, lies on the outside of the first intermediate stay 88 and is passed through a further slot 85 in the direction towards the inside 81, lies on the inside of the middle stay 86, passes round this through a further opening 85 and is passed outside in the direction towards the top of the foot, partially overlapping the hinged splint shank 11. The free end 51 can in this way be fastened by means of connecting elements 53 to the outside to the loop strap 50.

Figure 21:
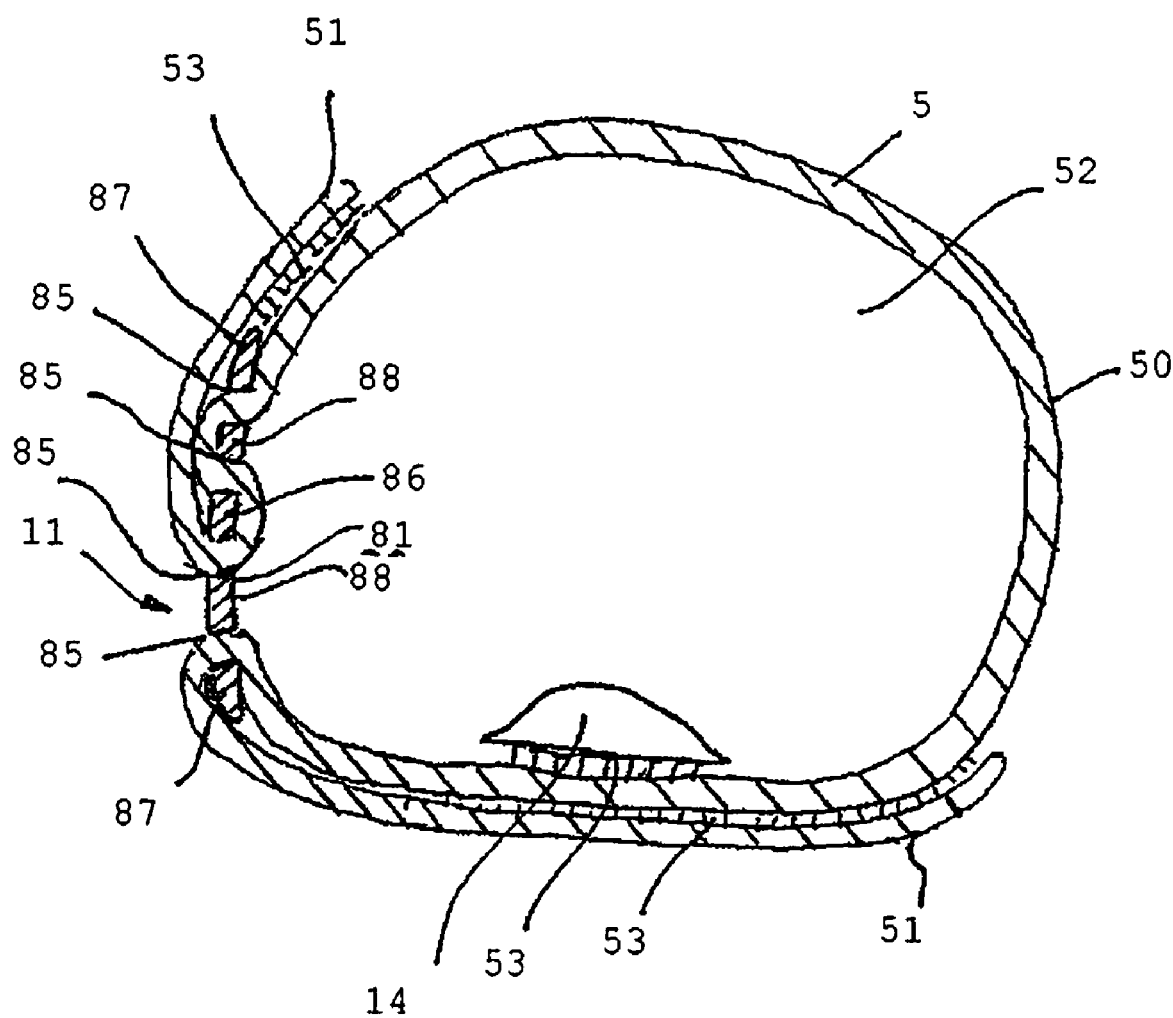
FIG. 21 A second cross-section through the shank of a hinged splint and the annular binding that belongs to it of the device according to the invention in the region of the central foot.

The annular binding routing in accordance with FIG. 21 has the advantage that the free ends will always be located at the outside of the loop strap 50, so that steps in the thickness of the material plus the connecting elements 51 are not created at the foot, thus avoiding pressure points at the foot. With this embodiment also it is of course possible for free ends at the top of the foot simply to be passed through one edge slot 85, so that it passes round the edge stay 87 and can be fastened at the outside to the loop body 50.

In this case the threading or looping of the annular binding 5 corresponds to that of annular binding 6 in the region of the big toe. In this embodiment again, it is possible for the pad 14 to be fastened, particularly in a manner that is easily released, using Velcro fasteners 53 to an inner side of the loop body 50 in the region of the underneath of the foot.

The non-rigid and, to a limited extent, floating attachment of the device 1 to the inner side of the foot has the advantage that the device 1 can adapt individually to the anatomical conditions, i.e., for instance, that the pivoting axis 12 of the hinged splint 9 can align itself automatically and continuously to the anatomical joint axis of the main big toe joint after the device 1 has been attached.

The invention claimed is:

1. An orthopaedic device for the correction of wrongly positioned toes, comprising:
   a first fastening provision for placement in a region of a big toe,
   a second fastening provision for placement in a region of a central foot, and
   a flexible splint, which is held by the first and second fastening provisions and which is adapted to extend along an inner side of the foot wherein the flexible splint is formed as a hinged flexible splint, articulated in a direction of flexion and extension of a toe or toes requiring correction, the flexible splint including a hinge mechanism adapted to be positioned on the main big toe joint and having a pivot axis that corresponds approximately to the joint axis of the main big toe joint in the direction of flexion and extension.

2. A device in accordance with claim 1 wherein the device includes a stocking for a foot that carries the first and second fastening provisions and the flexible splint.

3. A device in accordance with claim 2, wherein the stocking is open in a region of the toes.

4. A device in accordance with claim 2, wherein the device incorporates a holder for the big toe that is joined as one piece with the stocking or that is attached to the stocking.

5. A device in accordance with claim 4, wherein the holder for the big toe is adapted to fully enclose the big toe and which is open or closed at a free toe end.

6. A device in accordance with claim 2, wherein the device incorporates an annular binding for placement in the region of the central foot for entirely surrounding the central foot and connected to the stocking.

7. A device in accordance with claim 6, wherein a first annular binding surrounds the outside of the stocking in the region of the central foot.

8. A device in accordance with claim 7, wherein a second annular binding fully encloses the holder for the big toe in the region of the free end of the big toe, and is adapted to fully surround the big toe.

9. A device in accordance with claim 8, wherein the first and second annular bindings are formed of a flexible, supple material resistant to tension in the circumferential direction.

10. A device in accordance with claim 8, wherein in the region of one inner side of the foot both the first annular binding and the second annular binding in some areas are not joined to the stocking or to the holder for the big toe, so that between the first and second annular bindings and the holder for the big toe or the stocking, the first and second fastening provisions are formed.

11. A device in accordance with claim 10, wherein the fastening provisions consist of push-in pockets.

12. A device in accordance with claim 10, wherein the fastening provisions are formed as pouches sewn onto the stocking or fixed in some other way.

13. A device in accordance with claim 6, wherein the annular binding is joined to hinged splint shanks of the flexible splint.

14. A device in accordance with claim 6, wherein the annular binding incorporates loop straps and free ends.

15. A device in accordance with claim 2, wherein the stocking is a compression stocking.

16. A device in accordance with claim 1, wherein the flexible splint has hinged splint shanks whose three-dimensional form may or may not be planar.

17. A device in accordance with claim 16, wherein the hinged splint shanks have a lenticular cross-section.

18. A device in accordance with claim 16, wherein the hinged splint shanks each have a free end and a hinge end at the hinge mechanism.

19. A device in accordance with claim 18, wherein the hinge ends near the hinge mechanism have a three-dimensional form, and are formed so as to correspond to each other in such a way that the hinge end of one of the hinged splint shanks can be inserted into the hinge end of an other of the hinged splint shanks and interlock.

20. A device in accordance with claim 18, wherein the hinge ends of the hinged splint shanks have a form corresponding to one another with rotational symmetry about a pivot axis that corresponds approximately to the joint axis of the main big toe in the direction of flexion and extension.

21. A device in accordance with claim 16, wherein the hinged splint shanks are manufactured from thin, carbon-fibre reinforced plate.

22. A device in accordance with claim 16, wherein the hinged splint shanks have a three-dimensional form substantially that of a plate, longitudinally and laterally convex, having a first longitudinal boundary and a second longitudinal boundary as well as a narrow boundary.

23. A device in accordance with claim 22, wherein in the region of the longitudinal boundaries, and parallel to them, slots are provided, with the effect that a central stay, edge stays and intermediate stays are formed.

24. A device in accordance with claim 22, wherein the convexities of the hinged splint shanks are longitudinally and transversely adapted to the anatomical features of a foot.

25. A device in accordance with claim 1, wherein the flexible splint incorporates a first hinged splint shank and a second hinged splint shank which are able to pivot around an axis having an articulated connection through a hinge mechanism.

26. A device in accordance with claim 25, wherein the first hinged splint shank extends from the hinge mechanism to the first fastening provision and the second hinged splint shank extends to the second fastening provision.

27. A device in accordance with claim 25, wherein the hinge mechanism consists essentially of the first hinged splint shank, the second hinged splint shank and a hinged splint shank connecting mechanism.

28. A device in accordance with claim 25, wherein the hinged splint shanks and the hinge mechanism have a three-dimensional form adapted to the shape of the patient's foot.

29. A device in accordance with claim 25, wherein the hinge mechanism is formed as an annular hinge with a hinge ring and a hinge disk.

30. A device in accordance with claim 29, wherein the hinge ring is joined as one piece with the first hinged splint shank and/or the hinge disk is joined as one piece with the second hinged splint shank.

31. A device in accordance with claim 29, wherein an annular ridge is moulded onto the hinge disk, and this operates in combination with the hinge ring with the result that radial relationship of the hinge disk and of the hinge ring is maintained.

32. A device in accordance with claim 29, wherein for axial positioning of the hinge ring relative to the hinge disk engaging elements that operate together with a step, in particular an annular step, are provided.

33. A device in accordance with claim 25, wherein the hinged splint shanks have a material thickness that tapers towards each of the edge regions.

34. A device in accordance with claim 25, wherein the hinge mechanism is covered by a closing cap.

35. A device in accordance with claim 34, wherein the closing cap is connected to the hinged splint by engaging devices.

36. A device in accordance with claim 34, wherein the closing cap is joined to the first hinged splint shank.

37. A device in accordance with claim 34, wherein the closing cap is joined to the second hinged splint shank.

38. A device in accordance with claim 34, wherein the closing cap is formed as an axial bearing.

39. A device in accordance with claim 25, wherein the longitudinal extension of the hinged splint shanks enclose an angle $\alpha$ and $\beta$ with the pivot axis, and where the angles $\alpha$ and $\beta$ are chosen in such a way that the hinged splint can be placed against a patient's foot in such a way that the pivot axis of the hinge mechanism is approximately in line with the anatomical joint axis of the main big toe joint.

40. A device in accordance with claim 39, wherein the angle $\alpha$ is between 75° and 115°.

41. A device in accordance with claim 39, wherein the angle $\beta$ is between about 70° and 110°.

42. A device in accordance with claim 25, wherein annular bindings for placement around the central foot and around the big toe of the patient are positioned or threaded through the hinged splint shanks without creating steps.

43. A device in accordance with claim 42, wherein the annular bindings are fully threaded into the second hinged splint shank prior to application to the patient's foot.

44. A device in accordance with claim 25, wherein the device is not fixed rigidly to the foot, so that when worn the device can adapt the position of the hinge axis of the pivot mechanism individually to the anatomical features of the patient's foot.

45. A device in accordance with claim 1, wherein a foot-spreading pad is adapted to be used in an area of the sole of the foot behind the main joints of the toes for retrocapital support of the central foot.

46. A device in accordance with claim 1, wherein a force F1 can be exerted on the big toe in the direction of the inner side of the foot by the flexible splint for lateral correction of the big toe.

47. A device in accordance with claim 46, wherein there is a provision for exerting the force F1 on one or more neighbouring toes.

48. A device according to claim 47, wherein the provision consists of a toe holder for joining the big toe to one or more neighbouring toes of a foot.

49. A device in accordance with claim 1, wherein the surface regions of the flexible splint adapted to lie along the patient's foot are smooth.

50. A device in accordance with claim 1, wherein the flexible splint is manufactured from a plastic resistant to impact and not irritating to the skin.

51. A device in accordance with Claim 1, wherein the flexible splint comprises a first splint shank hinge end and a second splint shank with a second splint shank hinge end, and one of the first splint shank hinge end and the second splint shank hinge end comprises a first shape that is inserted into and interlocked with a second shape of an other of the first splint shank hinge end and the second splint shank hinge end.

* * * * *